US012194088B2

(12) United States Patent
Amara et al.

(10) Patent No.: US 12,194,088 B2
(45) **Date of Patent: *Jan. 14, 2025**

(54) COMPOSITIONS AND METHODS FOR PROMOTING IMMUNE RESPONSES TO HUMAN IMMUNODEFICIENCY VIRUS

(71) Applicants: Emory University, Atlanta, GA (US); Indian Institute of Science

(72) Inventors: Rama Rao Amara, Decatur, GA (US); Andrew Jones, Atlanta, GA (US); Raghavan Varadarajan, Bengaluru (IN)

(73) Assignees: Emory University, Atlanta, GA (US); Indian Institute of Science, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,940

(22) Filed: Jan. 24, 2023

(65) Prior Publication Data

US 2023/0233664 A1 Jul. 27, 2023

Related U.S. Application Data

(63) Continuation of application No. 16/966,387, filed as application No. PCT/US2019/016193 on Jan. 31, 2019, now Pat. No. 11,590,219.

(60) Provisional application No. 62/623,986, filed on Jan. 30, 2018.

(51) Int. Cl.
| | |
|---|---|
| *A61K 39/12* | (2006.01) |
| *A61K 39/21* | (2006.01) |
| *C07K 14/155* | (2006.01) |
| *C07K 14/16* | (2006.01) |
| *C12N 7/00* | (2006.01) |
| *A61K 39/00* | (2006.01) |

(52) U.S. Cl.
CPC ............ *A61K 39/21* (2013.01); *C07K 14/162* (2013.01); *C12N 7/00* (2013.01); *A61K 2039/53* (2013.01); *C12N 2710/24143* (2013.01); *C12N 2740/16034* (2013.01)

(58) Field of Classification Search
None
See application file for complete search history.

(56) References Cited

U.S. PATENT DOCUMENTS

| | | | |
|---|---|---|---|
| 6,911,205 | B2 | 6/2005 | Sodroski |
| 7,371,846 | B2 | 5/2008 | Hoxie |
| 11,590,219 | B2 | 2/2023 | Amara |
| 2005/0089526 | A1 | 4/2005 | Moore |
| 2011/0217338 | A1 | 9/2011 | Phogat |
| 2016/0040135 | A1 | 2/2016 | Moss |
| 2016/0159917 | A1 | 6/2016 | Bruenker |
| 2017/0233441 | A1 | 8/2017 | Kwong |

FOREIGN PATENT DOCUMENTS

| | | |
|---|---|---|
| WO | 2013085550 | 6/2013 |
| WO | 2017139392 | 8/2017 |

OTHER PUBLICATIONS

Bridge et al. Heterologous prime-boost-boost immunisation of Chinese cynomolgus macaques using DNA and recombinant poxvirus vectors expressing HIV-1 virus-like particles. Virology Journal 2011, 8:429.*

Lyer et al. Virus-Like Particles Displaying Trimeric Simian Immunodeficiency Virus (SIV) Envelope gp160 Enhance the Breadth of DNA/Modified Vaccinia Virus Ankara SIV Vaccine-Induced Antibody Responses in Rhesus Macaques. J Virol., 2016, 90:8842-8854.*

Kesavardhana et al. Structure-based Design of Cyclically Permuted HIV-1 gp120 Trimers That Elicit Neutralizing Antibodies. J. Biol. Chem., 2017, 292: 278-291.*

Lycke. Recent progress in mucosal vaccine development: potential and limitations. Nat. Rev. Immunol. 12, 592-605 (2012).*

Aran et al. An oral microjet vaccination system elicits antibody production in rabbits. Sci. Transl. Med. 9, eaaf6413 (2017).*

Aran et al. An oral microjet vaccination system elicits antibody production in rabbit, Sci. Transl. Med. 9, eaaf6413 (2017).

Iyer et al. Virus-Like Particles Displaying Trimeric Simian Immunodeficiency Virus (SIV) Envelope gp160 Enhance the Breadth of DNA/Modified Vaccinia Virus Ankara SIV Vaccine-Induced Antibody Responses in Rhesus Macaques, J Virol, 2016, 90:8842-8854.

Jones et al. A Trimeric HIV-1 Envelope gp120 Immunogen Induces Potent and Broad Anti-V1V2 Loop Antibodies against HIV-1 in Rabbits and Rhesus Macaques, J Virol, 2018, 92:e01796-17.

Jones et al. HIV-1 vaccination by needle-free oral injection induces strong mucosal immunity and protects against SHIV challenge, Nature Communications vol. 10, Article No. 798 (2019).

Kesavardhana et al. Structure-based Design of Cyclically Permuted HIV-1 gp120 Trimers That Elicit Neutralizing Antibodies, The Journal of Biological Chemistry, 2017, vol. 292, No. 1, pp. 278-291.

Korvacs et al. HIV-1 envelope trimer elicits more potent neutralizing antibody responses than monomeric gp120, Proc Natl Acad Sci U S A, 2012, 109(30):12111-6.

(Continued)

*Primary Examiner* — Nianxiang Zou

(74) *Attorney, Agent, or Firm* — Emory Patent Group

(57) ABSTRACT

This disclosure relates to methods of promoting immune responses against HIV and compositions related thereto. In certain embodiments, this disclosure relates to methods of vaccinating for HIV comprising administering to the subject a priming composition followed by a boosting composition. In certain embodiments, the priming composition comprises a recombinant virus such as recombinant MVA that encodes an Env protein of HIV or segment thereof. In certain embodiments, the boosting composition comprises a trimeric cyclically permuted gp120 chimeric protein reported herein or DNA encoding the same.

7 Claims, 9 Drawing Sheets

Specification includes a Sequence Listing.

(56) References Cited

OTHER PUBLICATIONS

Lycke, Recent progress in mucosal vaccine development: potential and limitations, Nat Rev Immunol, 2012, 12(8):592-605.
Saha et al. Designed Cyclic Permutants of HIV-1 gp120: Implications for Envelope Trimer Structure and Immunogen Design, Biochemistry, 2012, 51, 1836-1847.
Sahoo et al. A clade C HIV-1 vaccine protects against heterologous SHIV infection by modulating IgG glycosylation and T helper response in macaques, Sci Immunol. 2022, 7(73): eabl4102.

\* cited by examiner

| V2 Hotspot Binding (OD450) | | | | | | | | |
|---|---|---|---|---|---|---|---|---|
| 0.08 | 0.08 | 0.11 | 0.10 | 0.21 | 3.83 | 3.82 | 0.72 | JRFL E168K |
| 0.08 | 0.39 | 0.12 | 2.36 | 0.25 | 3.39 | 2.34 | 3.30 | ADA |
| 0.09 | 0.10 | 0.13 | 0.10 | 0.25 | 3.40 | 3.66 | 0.37 | SF162P3 |
| 0.06 | 0.06 | 0.09 | 0.08 | 0.21 | 1.06 | 0.51 | 0.24 | 1157 |
| 0.07 | 0.08 | 0.11 | 0.08 | 0.27 | 2.38 | 1.78 | 0.27 | 1157-Y173H |
| 0.06 | 0.06 | 0.08 | 0.06 | 0.17 | 3.46 | 3.64 | 0.30 | 1086.C |
| 33 | 34 | 35 | 36 | 33 | 34 | 35 | 36 | Animal # |
| MVA (2x) | | | | MVA (2x) cycP (2x) | | | | |

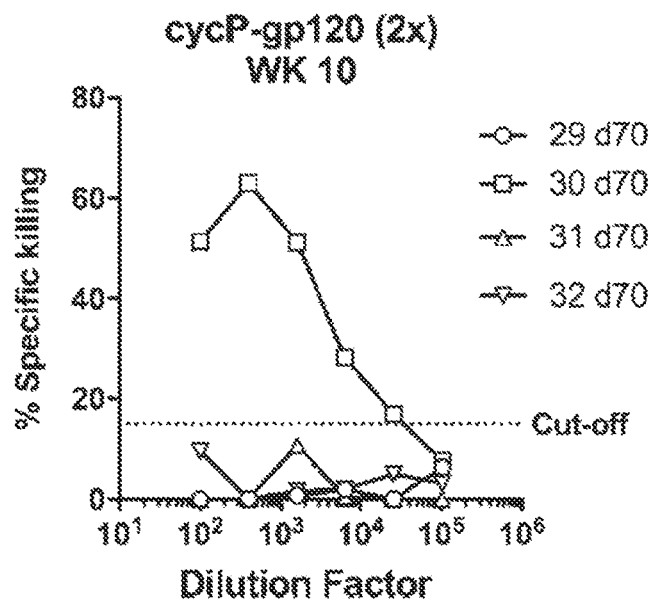
FIG. 2B
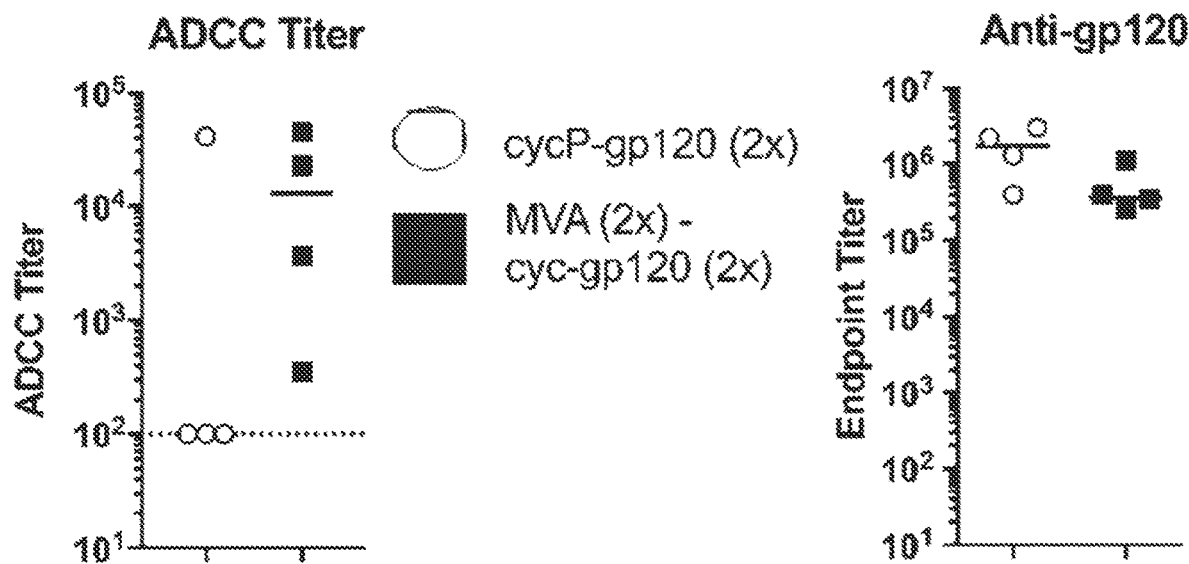
FIG. 2C
FIG. 2D

SEQ ID NO: 24

SEQUENCE LISTING

```
Sequence total quantity: 24
SEQ ID NO: 1            moltype = AA  length = 488
FEATURE                 Location/Qualifiers
source                  1..488
                        mol_type = protein
                        organism = synthetic construct
SEQUENCE: 1
EEDPCACESL VKFQAKVEGL LQALTRKLEA VSKRLAILEN TVVRSEGTME RGEIEISKNC    60
SFNITTSIRD EVQKEYALFY KLDVVPIDNN NTSYRLISCD TSVITQACPK ISFEPIPIHY   120
CAPAGFAILK CNDKTFNGKG PCKNVSTVQC THGIRPVVST QLLLNGSLAE EEVVIRSDNF   180
TNNAKTIIVQ LKESVEINCT RPNNNTRKSI HIGPGRAFYT TGEIIGDIRQ AHCNISRAKW   240
NDTLKQIVIK LREQFENKTI VFNHSSGGDP EIVMHSFNCG GEFFYCNSTQ LFNSTWNNNT   300
EGSNNTEGNT ITLPCRIKQI INMWQEVGKA MYAPPIRGQI RCSNITGLL LTRDGGINEN    360
GTEIFRPGGG DMRDNWRSEL YKYKVVKIEP LGVAPTKAKR RVVQREKRGS AGSAGSSRSA   420
GSAGSAGSEV VLENVTEHFN MWKNNMVEQM QEDIISLWDQ SLKPCVKLTP LCVTLNCKDV   480
NATNTTND                                                            488

SEQ ID NO: 2            moltype = AA  length = 503
FEATURE                 Location/Qualifiers
source                  1..503
                        mol_type = protein
                        organism = synthetic construct
SEQUENCE: 2
EEDPCACESL VKFQAKVEGL LQALTRKLEA VSKRLAILEN TVVASSEGTM MRGELKNCSF    60
NMTTELRDKK QKVYSLFYRL DVVQINENQG NRSNNSNKEY RLINCNTSAI TQACPKVSFE   120
PIPIHYCAPA GFAILCKCDK KFNGTGPCPS VSTVQCTHGI KPVVSTQLLL NGSLAEEEVM   180
IRSENITNNA KNILVQFNTP VQINCTRPNN NTRKSIRIGP GQAFYATGDI IGDIRQAHCN   240
VSKATWNETL GKVVKQLRKH FGNNTIIRFA NSSGGDLEVT THSFNCGGEF FYCNTSGLFN   300
STWISNTSVQ GSNSTGSNDS ITLPCRIKQI INMAAAWQRI GQAMYAPPIQ GVIRCVSNIT   360
GLILTRDGGS TNSTTETFRP GGGDMRDNWR SELYKYKVVK IEPLGVAPTR AKRRVVGREK   420
RGSAGSAGSS RSAGSAGSAG SEIHLENVTE EFNMWKNNMV EQMHTDIISL WDQSLKPCVK   480
LTPLCVTLQC TNVTNNITDD AAA                                          503

SEQ ID NO: 3            moltype = AA  length = 495
FEATURE                 Location/Qualifiers
source                  1..495
                        mol_type = protein
                        organism = synthetic construct
SEQUENCE: 3
EEDPCACESL VKFQAKVEGL LQALTRKLEA VSKRLAILEN TVVASSVNVT NGEEIKNCSF    60
NATTEIRDKK QKVYALFYRL DIVPLEEERK GNSSKYRLIN CNTSAITQAC PKVTFDPIPI   120
HYCAPAGYAI LKCNNKTFNG TGPCNNVSTV QCTHGIKPVV STQLLLNGSL AEGEIIIRSE   180
NLTNNVKTII VHLNESVEIV CTRPNNNTRK SIRIGPGQTF YATGDIIGNI RQAYCNIKKD   240
DWIRTLQRVG KKLAEHFPRR IINFTSPAGG DLEITTHSFN CRGEFFYCNT SSLFNSTYNP   300
NDTNSNSSSS NSSLDITIPC RIKQIINMWQ EVGRAMYAPP IEGNITCKSN ITGLLLVRDG   360
GVESNETEIF RPGGGDMRNN WRSELYKYKV VEIKPLGIAP TAAKRRVVER EKRGSAGSAG   420
SSRSAGSAGS AGSEMVLENV TENFNMWKND MVEQMHEDVI SLWDQSLKPC VKLTPLCVTL   480
ECRQVNTTNA TSAAA                                                   495

SEQ ID NO: 4            moltype = AA  length = 494
FEATURE                 Location/Qualifiers
source                  1..494
                        mol_type = protein
                        organism = synthetic construct
SEQUENCE: 4
EEDPCACESL VKFQAKVEGL LQALTRKLEA VSKRLAILEN TVVASSVNVT NGEVMKNCSF    60
NATTELKDKK HKVHALFYKL DVVPLNGNSS SSGEYRLINC NTSAITQACP KVSFDPIPLH   120
YCAPAGFAIL KCNNKTFNGT GPCRNVSTVQ CTHGIKPVVS TQLLLNGSLA EEEIIIRSEN   180
LTNNAKTIIV HLNESVNINC TRPNNNTRKS IRIGPGQTFY ATGDIIGNIR QAHCNINESK   240
WNNTLQKVGE ELAKHFPSKT IKFEPSSGGD LEITTHSFNC RGEFFYCNTS DLFNGTYRNG   300
TYNHTGRSSN GTITLQCKIK QIINMWQEVG RAIYAPPIEG EITCNSNITG LLLLRDGGQS   360
```

```
NETNDTETFR PGGGDMRDNW RSELYKYKVV EIKPLGVAPT EAKRRVVERE KRGSAGSAGS    420
SRSAGSAGSA GSEMVLANVT ENFNMWKNDM VEQMHEDIIS LWDESLKPCV KLTPLCVTLN    480
CTNVKGNESD TAAA                                                     494

SEQ ID NO: 5            moltype = AA   length = 486
FEATURE                 Location/Qualifiers
source                  1..486
                        mol_type = protein
                        organism = synthetic construct
SEQUENCE: 5
EEDPCACESL VKFQAKVEGL LQALTRKLEA VSKRLAILEN TVVASSVNVT NGEEIKNCSF     60
NTTTEIRDKK QKEYALFYRL DIVPLNEERK GNSSEYRLIN CNTSTITQAC PKVSFDPIPI    120
HYCAPAGYAI LKCNNKTFNG TGPCNNVSTV QCTHGIKPVV STQLLLNGSL AEEEIIIRSE    180
NLTNNAKTII VHLNESVEIN CTRPNNNTRK SIRIGPGQTF YATGDIIGDI RQAHCNISES    240
KWNKTLQRVS KKLKEHFPNK TIKFAPSSGG DLEITTHSFN CRGEFFYCNT SKLFNSTYNN    300
NTSNSTITLP CRIKQIINMW QEVGRAMYAP PIAGNITCKS NITGLLLTRD GGNNNNTTET    360
FRPGGGDMRD NWRSELYKYK VVEIKPLGIA PTKAKRRVVE REKRGSAGSA GSSRSAGSAG    420
SAGSEMVLEN VTENFNMWKN DMVDQMHEDT TSLWDQSLKP CVKLTPLCVT LNCTNVNVTN    480
ATSAAA                                                              486

SEQ ID NO: 6            moltype = AA   length = 43
FEATURE                 Location/Qualifiers
source                  1..43
                        mol_type = protein
                        organism = synthetic construct
SEQUENCE: 6
EEDPCACESL VKFQAKVEGL LQALTRKLEA VSKRLAILEN TVV                       43

SEQ ID NO: 7            moltype = AA   length = 6
FEATURE                 Location/Qualifiers
source                  1..6
                        mol_type = protein
                        organism = synthetic construct
SEQUENCE: 7
GGGGGG                                                                6

SEQ ID NO: 8            moltype = AA   length = 8
FEATURE                 Location/Qualifiers
source                  1..8
                        mol_type = protein
                        organism = synthetic construct
SEQUENCE: 8
PLCVTLNC                                                              8

SEQ ID NO: 9            moltype = AA   length = 5
FEATURE                 Location/Qualifiers
source                  1..5
                        mol_type = protein
                        organism = synthetic construct
SEQUENCE: 9
GGGGT                                                                 5

SEQ ID NO: 10           moltype = AA   length = 7
FEATURE                 Location/Qualifiers
source                  1..7
                        mol_type = protein
                        organism = synthetic construct
SEQUENCE: 10
SEGTMER                                                               7

SEQ ID NO: 11           moltype = AA   length = 6
FEATURE                 Location/Qualifiers
source                  1..6
                        mol_type = protein
                        organism = synthetic construct
SEQUENCE: 11
GGGPPP                                                                6

SEQ ID NO: 12           moltype = AA   length = 7
FEATURE                 Location/Qualifiers
source                  1..7
                        mol_type = protein
                        organism = synthetic construct
SEQUENCE: 12
NCSFNIT                                                               7

SEQ ID NO: 13           moltype = AA   length = 7
FEATURE                 Location/Qualifiers
source                  1..7
```

```
                            mol_type = protein
                            organism = synthetic construct
SEQUENCE: 13
GGGAPPP                                                                         7

SEQ ID NO: 14               moltype = AA    length = 7
FEATURE                     Location/Qualifiers
source                      1..7
                            mol_type = protein
                            organism = synthetic construct
SEQUENCE: 14
RDEVQKE                                                                         7

SEQ ID NO: 15               moltype = AA    length = 7
FEATURE                     Location/Qualifiers
source                      1..7
                            mol_type = protein
                            organism = synthetic construct
SEQUENCE: 15
KDKKHKV                                                                         7

SEQ ID NO: 16               moltype = AA    length = 5
FEATURE                     Location/Qualifiers
source                      1..5
                            mol_type = protein
                            organism = synthetic construct
SEQUENCE: 16
GGDRD                                                                           5

SEQ ID NO: 17               moltype = AA    length = 7
FEATURE                     Location/Qualifiers
source                      1..7
                            mol_type = protein
                            organism = synthetic construct
SEQUENCE: 17
HIGPGRA                                                                         7

SEQ ID NO: 18               moltype = AA    length = 15
FEATURE                     Location/Qualifiers
source                      1..15
                            mol_type = protein
                            organism = synthetic construct
SEQUENCE: 18
GNKMQKEYAL FYRLD                                                               15

SEQ ID NO: 19               moltype = AA    length = 7
FEATURE                     Location/Qualifiers
source                      1..7
                            mol_type = protein
                            organism = synthetic construct
SEQUENCE: 19
IIGDIRQ                                                                         7

SEQ ID NO: 20               moltype = AA    length = 485
FEATURE                     Location/Qualifiers
source                      1..485
                            mol_type = protein
                            organism = synthetic construct
SEQUENCE: 20
EEDPCACESL VKFQAKVEGL LQALTRKLEA VSKRLAILEN TVVASEGMME RGEIKNCSFN              60
ITKSIRNKVQ KEYALFYKLD VVPIDNKNNT KYRLISCNTS VITQACPKVS FEPIPIHYCA             120
PAGFAILKCN NKTFNGKGQC KNVSTVQCTH GIRPVVSTQL LLNGSLAEEK VVIRSDNFTD             180
NAKTIIVQLN ESVKINCTRP SNNTRKSIHI GPGRAFYTTG IIGDIRQAH CNISRAQWNN              240
TLKQIVEKLR EQFNNKTIVF THSSGGDPEI VMHSFNCGGE FFYCNSTQLF NSTWNDTEKS             300
SGTEGNDTII LPCRIKQIIN MWQEVGKAMY APPIKGQIRC SSNITGLLLT RDGGKNESEI             360
EIFRPGGGDM RDNWRSELYK YKVVKIEPLG VAPTKAKRRV VQREKRGSAG SAGSSRSAGS             420
AGSAGSEVVL ENVTEDFNMW KNNMVEQMQE DVINLWDQSL KPCVKLTPLC VTLNCKDVNA             480
TNTTS                                                                         485

SEQ ID NO: 21               moltype = AA    length = 421
FEATURE                     Location/Qualifiers
source                      1..421
                            mol_type = protein
                            organism = synthetic construct
SEQUENCE: 21
EVVLENVTEH FNMWKNNMVE QMQEDIISLW DQSLKPCVKL TPLCVTLNCK DVNATNTTND              60
SEGTMERGEI KNCSFNITTS IRDKVQKEYA LFYKLDVVPI DNNNTSYRLI SCDTSVITQA             120
CPKISFEPIP IHYCAPAGFA ILKCNDKTFN GKGPCKNVST VQCTHGIRPV VSTQLLLNGS             180
LAEEEVVIRS DNFTNNAKTI IVQLKESVEI NCTRPNNNTR KSIHIGPGRA FYTTGEIIGD             240
```

```
IRQAHCNISR AKWNDTLKQI VIKLREQFEN KTIVFNHSSG GDPEIVMHSF NCGGEFFYCN    300
STQLFNSTWN NNTEGSNNTE GNTITLPCRI KQIINMWQEV GKAMYAPPIR GQIRCSSNIT    360
GLLLTRDGGI NENGTEIFRP GGGDMRDNWR SELYKYKVVK IEPLGVAPTK AKRRVVQREK    420
R                                                                   421

SEQ ID NO: 22           moltype = AA  length = 15
FEATURE                 Location/Qualifiers
source                  1..15
                        mol_type = protein
                        organism = synthetic construct
SEQUENCE: 22
RDKVQKEYAL FYKLD                                                    15

SEQ ID NO: 23           moltype = AA  length = 15
FEATURE                 Location/Qualifiers
source                  1..15
                        mol_type = protein
                        organism = synthetic construct
SEQUENCE: 23
RDKVKKDYAL FYRLD                                                    15

SEQ ID NO: 24           moltype = AA  length = 197
FEATURE                 Location/Qualifiers
source                  1..197
                        mol_type = protein
                        organism = synthetic construct
SEQUENCE: 24
VXLTPLCVTL XCXXXXXXXX XXXXXXXXXX SYXXXXEXXX XNCSXNXTXX XDXXXXXXXL    60
FYXXDXVXXE XXXXXKXXXX XYRLXXCXTS XIXQACPKXX FXPIPIHYCX PAGXAILKXX   120
XXIRSXNXTX NXKXIIXXXX XXXIXCXRPX NNTRXSXXIG PGXXFYXTGX IXGDIRXAHC   180
NXSXXXWXXT LXXXXXX                                                 197
```

1

COMPOSITIONS AND METHODS FOR PROMOTING IMMUNE RESPONSES TO HUMAN IMMUNODEFICIENCY VIRUS

CROSS-REFERENCE TO RELATED APPLICATIONS

This application is a continuation of U.S. application Ser. No. 16/966,387 filed Jul. 30, 2020, which is the National Stage of International Application No. PCT/US2019/016193 filed Jan. 31, 2019, which claims the benefit of U.S. Provisional Application No. 62/623,986 filed Jan. 30, 2018. The entirety of each of these applications is hereby incorporated by reference for all purposes.

STATEMENT REGARDING FEDERALLY SPONSORED RESEARCH OR DEVELOPMENT

This invention was made with government support under AI109633 and DE026333 awarded by the National Institutes of Health. The government has certain rights in the invention.

INCORPORATION-BY-REFERENCE OF MATERIAL SUBMITTED AS AN XML FILE VIA THE OFFICE ELECTRONIC FILING SYSTEM

The Sequence Listing associated with this application is provided in XML format and is hereby incorporated by reference into the specification. The name of the XML file containing the Sequence Listing is 17220USCON.xml. The XML file is 25 KB, was created on Jan. 18, 2023, and is being submitted electronically via the USPTO patent electronic filing system.

BACKGROUND

There are millions of humans living with HIV/AIDS. Combination antiretroviral therapy (cART) treatment regimens have successfully prolonged the lives of infected individuals. However, there is a great need to develop a safe and effective HIV vaccine to reduce the spread of HIV infections. Developing vaccines for HIV has been challenging. Stopping combination antiretroviral therapy (cART) leads to the re-emergence. Immune privileged areas are able to shield HIV from the immune system. See Churchill et al., Nat Rev Microbiol. 2016, 14:55-60.

HIV-1 has surface spikes made up of trimeric viral envelope glycoprotein (Env) proteins containing a membrane-anchored subunit gp41 and surface subunit gp120. Subunit gp120 undergoes conformational changes upon interaction with CD4. Further binding of gp120 to CCR5 and/or CXCR4 in target cell membranes leads to invasion of HIV into the cells by the fusion of the viral and cellular membranes. HIV-1 is reported to be stabilized by interactions between V1-V3 loops at the apex of the trimer spikes. See Julien et al. Science, 2013, 342(6165):1477-83.

Initial HIV vaccines candidates consisted of gp120 subunits. These vaccines elicited antibody responses in all of vaccinated participants, but it was ineffective in preventing HIV-1 infection. More recently, a clinical trial for HIV vaccination, referred to as RV144, involved recombinant canarypox vector (ALVAC-HIV) plus two recombinant gp120 boosts (AIDSVAX B/E). ALVAC-HIV is a live recombinant canarypox vector vaccine that expresses HIV-1 gag, protease, and gp120 linked to the transmembrane anchoring portion of gp41. A post hoc analysis in vaccine efficacy revealed an early peak in vaccine efficacy in the first year, which declined thereafter. See Robb et al. Lancet Infect Dis. 2012, 12:531-537. It is reported that viral evolution was a response to the RV144 HIV vaccination suggesting immune pressure is exerted on the HIV virus. See Gao et al, Viruses, 2018, 10(4), pii: E167. Haynes et al. report an increased rate of infection among vaccine recipients with high levels of Env-specific IgA antibodies, as compared with other vaccine recipients. N Engl J Med. 2012, 366(14):1275-1286.

Saha et al. report circularly permuted gp120 fusion peptides in a trimeric conformation. Biochemistry, 2012, 51, 1836-1847. Trimerization was achieved by fusion of gp120 with a trimerization domain (h-CMP or SUMO2a) inserted into the V1 loop. See also Kesavardhana et al. J Biol Chem. 2017, 292(1):278-291. Jones et al. report using a circularly permuted gp120 fusion in a trimeric conformation as an immunogen in a method that induces potent and broad anti-V1V2 loop antibodies against HIV-1 in rabbits and rhesus macaques. J Virol. 2018, 92(5), e01796-17.

References cited herein are not an admission of prior art.

SUMMARY

This disclosure relates to methods of promoting immune responses against HIV and compositions related thereto. In certain embodiments, this disclosure relates to methods of vaccinating for HIV comprising administering to the subject a priming composition followed by a boosting composition. In certain embodiments, the priming composition comprises a recombinant virus such as recombinant MVA that encodes an Env protein of HIV or segment thereof. In certain embodiments, the boosting composition comprises a trimeric cyclically permuted gp120 chimeric protein reported herein or DNA encoding the same.

In certain embodiments, this disclosure relates to methods of vaccinating or immunizing comprising: i) administering to a human subject a nucleic acid and/or recombinant virus that encodes an HIV Env protein or segment thereof under conditions such that virus-like particles with surface gp120 proteins are formed in the subject; and ii) administering to the human subject an effective amount of a trimeric cyclically permuted gp120 reported herein or combination of trimeric protein complexes.

In certain embodiments, this disclosure relates to methods of vaccinating or immunizing comprising: i) administering to a human subject a nucleic acid and/or recombinant virus that encodes an HIV Env protein or segment thereof under conditions such that virus-like particles with surface gp120 proteins are formed in the subject; and ii) administering to the human subject an effective amount of nucleic acid encoding a chimeric protein that forms trimeric cyclically permuted gp120 reported herein or combinations of trimeric protein complexes.

In certain embodiments, the trimeric complex comprises chimeric proteins comprising a first segment of HIV variable domain 1, a second segment of HIV variable domain 1, an HIV variable domain 2, and an HIV variable domain 3, and a trimerization domain; wherein the trimerization domain is attached through N-terminus of the second segment of HIV variable domain 1, and wherein the first segment of HIV variable domain 1 is attached through the C-terminus of HIV variable domain 3.

In certain embodiments, administering to the human subject an effective amount of a trimeric cyclically permuted gp120 chimeric protein complex or nucleic acid encoding the same is more than one week, two weeks, three weeks, or four weeks after administering to a human subject a nucleic acid or recombinant virus that encodes HIV Env protein or segment thereof.

In certain embodiments, administering is to the skin, muscle, or buccal cavity. In certain embodiments, administration is by syringe, microneedle, topically, or using pressurized devices, e.g., device comprising a nozzle to push a solution into tissue by means of pressure, e.g., spring or gas powered without the use of a needle (needle-free devices). In certain embodiments, administering is by propelling liquid or particles through the skin or soft tissue lining of the mouth with pressure. In certain embodiments, administering is buccal, sublingual, intra-nasal, intra-gastric, intra-rectal, or intra-vaginal.

In certain embodiments this disclosure contemplates pharmaceutical compositions comprising chimeric proteins disclosed herein and variants thereof.

In certain embodiments, this disclosure relates to methods of vaccinating or immunizing comprising: administering to the human subject an effective amount of a trimeric cyclically permuted gp120 or combination of trimeric protein complexes, optionally in combination with a nucleic acid and/or recombinant virus that encodes an HIV Env protein or segment thereof.

In certain embodiments, this disclosure contemplates nucleic acids, recombinant vectors, viral vectors, and bacterial plasmids encoding chimeric proteins disclose herein which form trimeric cyclically permuted gp120 or combination of trimeric protein complexes and uses in priming and boosting methods disclosed herein. In certain embodiments, this disclosure relates to cells and other expression vectors and expression systems for use in producing chimeric proteins and trimeric cyclically permuted gp120 sequences or variants reported herein.

BRIEF DESCRIPTION OF THE DRAWINGS

FIG. 2B shows data in rabbits immunized with cycP-gp120 or MVA-HIV prime/cycP-gp120 boost. ADCC activity against JRFL-infected target cells was measured against sera from weeks 10, 18, and 34 in rabbits immunized with MVA-HIV followed by boosting with cycP-gp120 and week 10 from rabbits immunized with cycP-gp120 alone. Percent specific killing values were subtracted from week 0 sera to remove background ADCC activity.

FIG. 2C shows ADCC titer comparison between cycP-gp120 (2×)- and MVA-HIV (2×)- and cycP-gp120 (2×)- immunized rabbits. ADCC Ab titers were defined as the reciprocal of the highest dilution indicating a positive response.

FIG. 2D shows data on anti-gp120 serum IgG titer.

DETAILED DISCUSSION

Figure 1A:
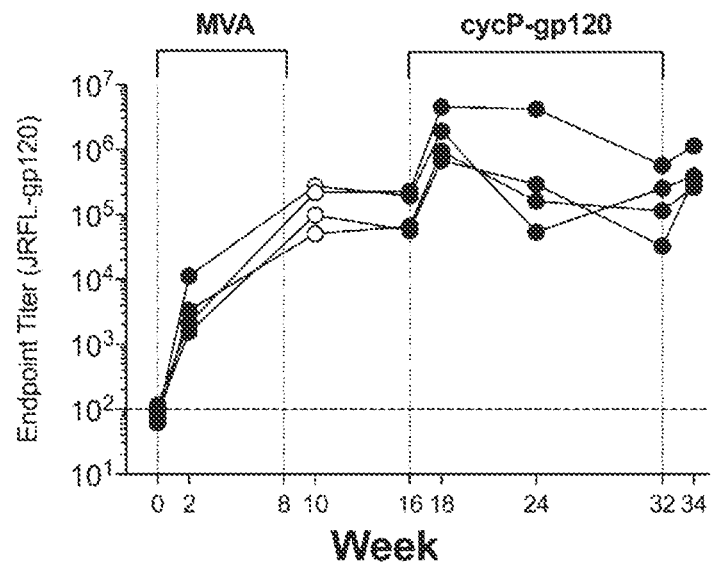
FIG. 1A shows kinetic analysis of JRFL-gp120-specific IgG endpoint titers measured via ELISA. MVA-primed rabbits were boosted with cycP-gp120, which results in the presence of neutralizing antibodies, including increased gp120/gp140 and gp70-V1V2-directed antibodies. Rabbits were immunized twice with MVA-HIV at weeks 0 and 8 and boosted with cycP-gp120 protein at weeks 16 and 32.
Figure 1B:
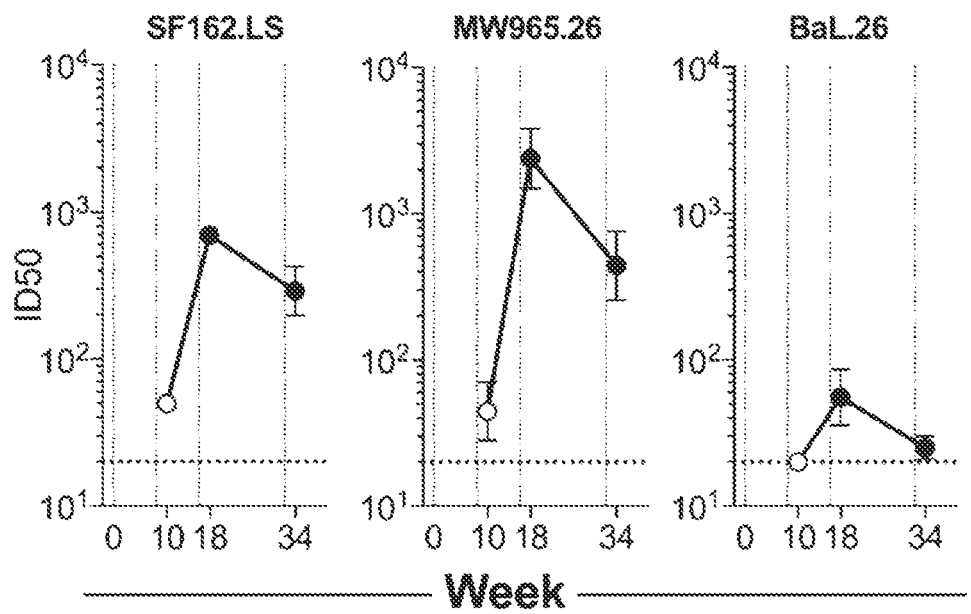
FIG. 1B shows data on neutralizing antibodies measured at weeks 10, 18, and 34 against tier-1A and -1B viruses, reported as ID50 concentrations.

Before the present disclosure is described in greater detail, it is to be understood that this disclosure is not limited to embodiments described, and as such may, of course, vary. It is also to be understood that the terminology used herein is for describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

"Subject" refers to any animal, preferably a human patient, livestock, rodent, monkey or domestic pet. The term is used herein to encompasses apparently healthy, non-HIV-infected individuals or a patient who is known to be infected with, diagnosed with, a pathogen (e.g., an HIV of any clade).

As used herein, the term "combination with" when used to describe administration with an additional treatment means that the agent may be administered prior to, together with, or after the additional treatment, or a combination thereof.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a rage of amino acids expressly specified in the claim. In certain embodiments, the disclosure contemplates that the "N-terminus of a peptide may consist of an amino acid sequence," which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

The terms "protein" and "peptide" refer to polymers comprising amino acids joined via peptide bonds and are used interchangeably. Amino acids may be naturally or non-naturally occurring. A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that are contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids. Contemplated chimeric proteins include those with self-cleaving peptides such as P2A-GSG. See Wang. Scientific Reports 5, Article number: 16273 (2015).

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, this disclosure contemplates that chimeric proteins disclosed herein may be variants. Variants may include 1 or 2 amino acid substitutions or conserved substitutions. Variants may include 3 or 4 amino acid substitutions or conserved substitutions. Variants may include 5 or 6 or more amino acid substitutions or conserved substitutions. Variant include those with not more than 1% or 2% of the amino acids are substituted. Variant include those with not more than 3% or 4% of the amino acids are substituted. Variants include proteins with greater than 80%, 89%, 90%, 95%, 98%, or 99% identity or similarity.

Variant peptides can be produced by mutating a vector to produce appropriate codon alternatives for polypeptide translation. Active variants and fragments can be identified with a high probability using computer modeling. Shihab et al. report an online genome tolerance browser. BMC Bioinformatics, 2017, 18(1):20. Ng et al. report methods of predicting the effects of amino acid substitutions on protein function. Annu Rev Genomics Hum Genet, 2006, 7:61-80. Teng et al. Approaches and resources for prediction of the effects of non-synonymous single nucleotide polymorphism on protein function and interactions. Curr Pharm Biotechnol, 2008, 9(2):123-33.

Desired amino acid substitutions (whether conservative or non-conservative) can be determined by those skilled in the art at the time such substitutions are desired. Guidance in determining which and how many amino acid residues may be substituted, inserted or deleted without abolishing biological activity may be found using computer programs well known in the art, for example, RaptorX, ESyPred3D, HHpred, Homology Modeling Professional for HyperChem, DNAStar, SPARKS-X, EVfold, Phyre, and Phyre2 software. See also Saldano et al. Evolutionary Conserved Positions Define Protein Conformational Diversity, PLoS Comput Biol. 2016, 12(3):e1004775; Marks et al. Protein structure from sequence variation, Nat Biotechnol. 2012, 30(11): 1072-80; Mackenzie et al. Curr Opin Struct Biol, 2017, 44:161-167 Mackenzie et al. Proc Natl Acad Sci USA. 113(47):E7438-E7447 (2016); Joseph et al. J R Soc Interface, 2014, 11(95):20131147, Wei et al. Int. J. Mol. Sci. 2016, 17(12), 2118. Variants can be tested in functional assays. Certain variants have less than 10%, and preferably less than 5%, and still more preferably less than 2% changes (whether substitutions, deletions, and so on).

Sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 7) and GGGGT (SEQ ID NO: 9) have a sequence identity of 4 out of 5 or 80%. For example, the polypeptides GGGPPP (SEQ ID NO: 11) and GGGAPPP (SEQ ID NO: 13) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q. The amino acid groups are also considered conserved substitutions.

Percent identity can be determined, for example, by comparing sequence information using the GAP computer program, version 6.0, available from the University of Wisconsin Genetics Computer Group (UWGCG). The GAP program utilizes the alignment method of Needleman and Wunsch (J Mol Biol 1970 48:443), as revised by Smith and Waterman (Adv Appl Math 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (Nucl Acids Res 1986 14:6745), as described by Schwartz and Dayhoff (eds., Atlas of Protein Sequence and Structure, National Biomedical Research Foundation, Washington, D.C. 1979, pp. 353-358); (2) a penalty of 3.0 for each gap and an additional 0.10 penalty for each symbol in each gap; and (3) no penalty for end gaps.

The term "recombinant vector" when made in reference to vectors and nucleic acids refers to a nucleic acid molecule that is comprised of segments of nucleic acid joined together by means of molecular biological techniques. The term recombinant nucleic acid is distinguished from the natural recombinants that result from crossing-over between homologous chromosomes. Recombinant nucleic acids as used herein are an unnatural union of nucleic acids from nonhomologous sources, usually from different organisms.

The terms "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

In certain embodiments, a vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vector, these extracts and components can synthesize proteins of interest. Cell-free systems typically do not contain proteases and enable labelling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferaseI (galT), feedback-insensitive α subunit of anthranilate synthase (OASA1D), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

Methods of Use

In certain embodiments, this disclosure relates to methods of vaccinating or immunizing for HIV comprising administering to the subject a priming composition followed by a boosting composition. In certain embodiments, the priming composition comprises a recombinant virus such as recombinant MVA that encodes an Env protein of HIV or segment thereof. In certain embodiments, the boosting composition comprises a trimeric cyclically permuted gp120 reported herein or a nucleic acid encoding a chiral protein that forms a trimeric cyclically permuted gp120 reported herein, or combinations of trimeric cyclically permuted gp120 reported herein.

In certain embodiments, this disclosure relates to methods of vaccinating or immunizing comprising: i) administering to a human subject a nucleic acid and/or recombinant virus that encodes an HIV Env protein or segment thereof under conditions such that virus-like particles with surface gp120 proteins are formed in the subject; and ii) administering to the human subject an effective amount of a trimeric cyclically permuted gp120 reported herein or combination of trimeric protein complexes or a nucleic acid encoding a chiral protein that forms a trimeric cyclically permuted gp120 reported herein or combinations of trimeric cyclically permuted gp120 reported herein.

In certain embodiments, the methods are conducted in combination with an adjuvant.

In certain embodiments, administering to the human subject an effective amount of a trimeric protein complex is more than one week, two weeks, three weeks, or four weeks after administering to a human subject a nucleic acid or recombinant virus that encodes HIV Env protein or segment thereof.

In certain embodiments, administering to the human subject an effective amount of a trimeric protein complex is more than one week, two weeks, three weeks, or four weeks before administering to a human subject a nucleic acid and/or recombinant virus that encodes HIV Env protein or segment thereof.

In certain embodiments, administering is to the skin, muscle, or buccal cavity. In certain embodiments, administration is by syringe, microneedle, topically, or using pressurized devices, e.g., device comprising a nozzle to push a solution into tissue by means of pressure, e.g., spring-powered without the use of a needle (needle-free devices).

DNA-based vaccines typically use bacterial plasmids to express protein immunogens in vaccinated hosts. Recombinant DNA technology is used to clone cDNAs encoding immunogens of interest into eukaryotic expression plasmids. Vaccine plasmids are then amplified in bacteria, purified, and directly inoculated into the hosts being vaccinated. DNA typically is inoculated by a needle injection of DNA in saline, or by a gene gun device that delivers DNA-coated gold beads into skin. The plasmid DNA is taken up by host cells, the vaccine protein is expressed, processed and presented in the context of self-major histocompatibility (MIC) class I and class II molecules, and an immune response against the DNA-encoded immunogen is generated.

In certain embodiments the present disclosure is a method to generate an immune response against HIV gp120 antigen. Such a response can be a CD8+ T cell immune response or an antibody response. More particularly, the present disclosure relates to "prime and boost" immunization regimes in which the immune response induced by administration of a priming composition is boosted by administration of a boosting composition. The present disclosure is based on experimental demonstration that effective priming can be achieved using modified vaccinia Ankara (MVA) vectors, following boosting with trimeric cyclically permuted gp120 that contain chimeric proteins disclosed herein.

A major protective component of the immune response against a number of pathogens is mediated by T lymphocytes of the CD8+ type, also known as cytotoxic T lymphocytes (CTL). An important function of CD8+ cells is secretion of gamma interferon (IFNγ), and this provides a measure of CD8+ T cell immune response. A second component of the immune response is antibody directed to the proteins of the pathogen.

The present disclosure employs trimeric cyclically permuted gp120 that contain chimeric proteins disclosed herein which has been found to be an effective means for providing a boost to a CD8+ T cell immune response primed to antigen using any of a variety of different priming compositions and also eliciting an antibody response.

Notably, use of predecessors of the present disclosure allows for trimeric cyclically permuted gp120 that contain chimeric protein disclosed herein to boost a CD8+ T cell immune response primed by a DNA vaccine and/or recombinant virus/recombinant MVA vaccine and also eliciting an antibody response. The trimeric cyclically permuted gp120 that contain chimeric protein disclosed herein may be found to induce a CD8+ T cell response after immunization.

Non-human primates immunized with plasmid DNA and boosted with the MVA were effectively protected against intramucosal challenge with live virus (Amara et al 2001 Science 292:69-74). Advantageously, it is contemplated that a vaccination regime using needle-free, intradermal, intramuscular, or mucosal immunization for both prime and boost can be employed, constituting a general immunization regime suitable for inducing CD8+ T cells and also eliciting an antibody response, e.g., in humans. An immune response to an HIV antigen may be primed by immunization with plasmid DNA, recombinant virus, or by infection with an infectious agent.

A further aspect of this disclosure provides a method of inducing a CD8+ T cell immune response to an HIV antigen in an individual, and also eliciting an antibody response, the method comprising administering to the individual a priming composition comprising nucleic acid encoding the HIV gp120 antigen and then administering a boosting composition which comprises trimeric cyclically permuted gp120 that contain chimeric proteins disclosed herein or nucleic acids encoding the same.

A further aspect provides for use of trimeric cyclically permuted gp120 that contain chimeric proteins as disclosed, in the manufacture of a medicament for administration to a mammal to boost a CD8+ T cell immune response to an HIV gp120 antigen, and also eliciting an antibody response. Such a medicament is generally for administration following prior administration of a priming composition comprising nucleic acid and/or recombinant virus encoding the antigen.

The priming composition may comprise DNA encoding the HIV gp120 antigen or trimeric cyclically permuted gp120 disclosed herein, such DNA being in the form of a circular plasmid that is not capable of replicating in mammalian cells. Any selectable marker should preferably not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

In particular embodiments of the various aspects of the present disclosure, administration of a priming composition is followed by boosting with a boosting composition, or first and second boosting compositions, the first and second boosting compositions being the same or different from one another. In one embodiment, a triple immunization regime employs DNA, then recombinant virus, followed by a further (third) boosting composition comprising a trimeric cyclically permuted gp120 that contain chimeric protein disclosed herein. Another option is DNA then MVA then adenovirus, optionally followed by subsequent boosting administration composition comprising trimeric cyclically permuted gp120 that contains chimeric protein disclosed herein.

The antigen to be encoded in respective priming compositions (however many boosting compositions are employed) need not be identical. The antigen may correspond to a complete HIV pg120 antigen, or a fragment thereof. Peptide epitopes or artificial strings of epitopes may be employed, more efficiently cutting out unnecessary protein sequence in the antigen and encoding sequence in the vector or vectors. One or more additional epitopes may be included, for instance epitopes which are recognized by T helper cells, especially epitopes recognized in individuals of different HLA types.

An HIV antigen of the disclosure to be encoded by a recombinant virus/recombinant MVA includes polypeptides having immunogenic activity elicited by an amino acid sequence of an HIV Env, Gag. Pol, Vif Vpr, Tat, Rev, Vpu, or Nef amino acid sequence as at least one CD8+ T cell epitope. This amino acid sequence substantially corresponds to at least one 10-900 amino acid fragment and/or consensus sequence of a known HIV Env or Pol; or at least one 10-450 amino acid fragment and/or consensus sequence of a known HIV Gag; or at least one 10-100 amino acid fragment and/or consensus sequence of a known HIV Vif, Vpr, Tat, Rev, Vpu, or Nef.

Although a full-length Env precursor sequence is presented for use in the present disclosure, Env is optionally deleted of subsequences. For example, regions of the gp120 surface and gp41 transmembrane cleavage products can be deleted.

Although a full-length Gag precursor sequence is presented for use in the present disclosure, Gag is optionally deleted of subsequences. For example, regions of the matrix protein (p17), regions of the capsid protein (p24), regions of the nucleocapsid protein (p7), and regions of p6 (the C-terminal peptide of the Gag polyprotein) can be deleted.

Although a full-length Pol precursor sequence is presented for use in the present disclosure, Pol is optionally deleted of subsequences. For example, regions of the protease protein (p10), regions of the reverse transcriptase protein (p66/p51), and regions of the integrase protein (p32) can be deleted.

Such an HIV Env, Gag, or Pol can have overall identity of at least 50% to a known Env, Gag, or Pol protein amino acid sequence, such as 50-99% identity, or any range or value therein, while eliciting an immunogenic response against at least one strain of an HIV.

Cyclically Permuted HIV-1 gp120 Trimers

Cyclically permutated HIV-1 gp120 trimers are trimeric protein complexes having chimeric proteins. The chimeric proteins contain a trimerization domain and segments of HIV variable domains 1, 2, and 3.

In certain embodiments, the trimeric complex comprises chimeric proteins comprising a first segment of HIV variable domain 1, a second segment of HIV variable domain 1, an HIV variable domain 2, and an HIV variable domain 3, and a trimerization domain; wherein the trimerization domain is attached through N-terminus of the second segment of HIV variable domain 1, and wherein the first segment of HIV variable domain 1 is attached through the C-terminus of HIV variable domain 3.

The sequences of (cycP-gp120) JRFL-hCMP-V1cyc and JRCSF-hCMP-V1cyc are reported in Kesavrhana et al., J Biol Chem, 2017, 292(1):278-291:

(SEQ ID NO: 1)
EEDPCACESLVKFQAKVEGLLQALTRKLEAVSKRLAILENTVVRSEGTM
ERGEIEISKNCSFNITTSIRDEVQKEYALFYKLDVVPIDNNNTSYRLIS
CDTSVITQACPKISFEPIPIHYCAPAGFAILKCNDKTFNGKGPCKNVST
VQCTHGIRPVVSTQLLLNGSLAEEEVVIRSDNFTNNAKTIIVQLKESVE
INCTRPNNNTRKSIHIGPGRAFYTTGEIIGDIRQAHCNISRAKWNDTLK
QIVIKLREQFENKTIVFNHSSGGDPEIVMHSFNCGGEFFYCNSTQLFNS
TWNNNTEGSNNTEGNTITLPCRIKQIINMWQEVGKAMYAPPIRGQIRCS
SNITGLLLTRDGGINENGTEIFRPGGGDMRDNWRSELYKYKVVKIEPLG
VAPTKAKRRVVQREKRGSAGSAGSSRSAGSAGSAGSEVVLENVTEHFNM
WKNNMVEQMQEDIISLWDQSLKPCVKLTPLCVTLNCKDVNATNTTND
(cycP-gp120) JRFL-hCMP-V1cyc;

(SEQ ID NO: 20)
EEDPCACESLVKFQAKVEGLLQALTRKLEAVSKRLAILENTVVASEGMM
ERGEIKNCSFNITKSIRNKVQKEYALFYKLDVVPIDNKNNTKYRLISCN
TSVITQACPKVSFEPIPIHYCAPAGFAILKCNNKTFNGKGQCKNVSTVQ
CTHGIRPVVSTQLLLNGSLAEEKVVIRSDNFTDNAKTIIVQLNESVKIN
CTRPSNNTRKSIHIGPGRAFYTTGEIIGDIRQAHCNISRAQWNNTLKQI
VEKLREQFNNKTIVFTHSSGGDPEIVMHSFNCGGEFFYCNSTQLFNSTW
NDTEKSSGTEGNDTIILPCRIKQIINMWQEVGKAMYAPPIKGQIRCSSN
ITGLLLTRDGGKNESEIEIFRPGGGDMRDNWRSELYKYKVVKIEPLGVA
PTKAKRRVVQREKRGSAGSAGSSRSAGSAGSAGSEVVLENVTEDFNMWK
NNMVEQMQEDVINLWDQSLKPCVKLTPLCVTLNCKDVNATNTTS
JRCSF-hCMP-V1cyc;

(SEQ ID NO: 21)
EVVLENVTEHFNMWKNNMVEQMQEDIISLWDQSLKPCVKLTPLCVTLNC
KDVNATNTTNDSEGTMERGEIKNCSFNITTSIRDKVQKEYALFYKLDVV
PIDNNNTSYRLISCDTSVITQACPKISFEPIPIHYCAPAGFAILKCNDK
TFNGKGPCKNVSTVQCTHGIRPVVSTQLLLNGSLAEEEVVIRSDNFTNN
AKTIIVQLKESVEINCTRPNNNTRKSIHIGPGRAFYTTGEIIGDIRQAH
CNISRAKWNDTLKQIVIKLREQFENKTIVFNHSSGGDPEIVMHSFNCGG
EFFYCNSTQLFNSTWNNNTEGSNNTEGNTITLPCRIKQIINMWQEVGKA
MYAPPIRGQIRCSSNITGLLLTRDGGINENGTEIFRPGGGDMRDNWRSE
LYKYKVVKIEPLGVAPTKAKRRVVQREKR JRFL-gp120

In certain embodiments, the cyclically permutated HIV-1 gp120 trimer or chimeric proteins comprises an amino acid sequence:

(SEQ ID NO: 1)
EEDPCACESLVKFQAKVEGLLQALTRKLEAVSKRLAILENTVVRSEGTM
ERGEIEISKNCSFNITTSIRDEVQKEYALFYKLDVVPIDNNNTSYRLIS
CDTSVITQACPKISFEPIPIHYCAPAGFAILKCNDKTFNGKGPCKNVST
VQCTHGIRPVVSTQLLLNGSLAEEEVVIRSDNFTNNAKTIIVQLKESVE
INCTRPNNNTRKSIHIGPGRAFYTTGEIIGDIRQAHCNISRAKWNDTLK

QIVIKLREQFENKTIVFNHSSGGDPEIVMHSFNCGGEFFYCNSTQLFNS
TWNNNTEGSNNTEGNTITLPCRIKQIINMWQEVGKAMYAPPIRGQIRCS
SNITGLLLTRDGGINENGTEIFRPGGGDMRDNWRSELYKYKVVKIEPLG
VAPTKAKRRVVQREKRGSAGSAGSSRSAGSAGSAGSEVVLENVTEHFNM
WKNNMVEQMQEDIISLWDQSLKPCVKLTPLCVTLNCKDVNATNTTND or variant thereof JRFL-CYCP (clade B).

In certain embodiments, the chimeric proteins comprises an amino acid sequence (SEQ ID NO: 2)
EEDPCACESLVKFQAKVEGLLQALTRKLEAVSKRLAILENTVVASSEGT
MMRGELKNCSFNMTTELRDKKQKVYSLFYRLDVVQINENQGNRSNNSNK
EYRLINCNTSAITQACPKVSFEPIPIHYCAPAGFAILKCKDKKFNGTGP
CPSVSTVQCTHGIKPVVSTQLLLNGSLAEEEVMIRSENITNNAKNILVQ
FNTPVQINCTRPNNNTRKSIRIGPGQAFYATGDIIGDIRQAHCNVSKAT
WNETLGKVVKQLRKHFGNNTIIRFANSSGGDLEVTTHSFNCGGEFFYCN
TSGLFNSTWISNTSVQGSNSTGSNDSITLPCRIKQIINMAAAWQRIGQA
MYAPPIQGVIRCVSNITGLILTRDGGSTNSTTETFRPGGGDMRDNWRSE
LYKYKVVKIEPLGVAPTRAKRRVVGREKRGSAGSAGSSRSAGSAGSAGS
EIHLENVTEEFNMWKNNMVEQMHTDIISLWDQSLKPCVKLTPLCVTLQC
TNVTNNITDDAAA or variant thereof, BG505-CycP (clade A).

In certain embodiments, the chimeric proteins comprises an amino acid sequence (SEQ ID NO: 3)
EEDPCACESLVKFQAKVEGLLQALTRKLEAVSKRLAILENTVVASSVNV
TNGEEIKNCSFNATTEIRDKKQKVYALFYRLDIVPLEEERKGNSSKYRL
INCNTSAITQACPKVTFDPIPIHYCAPAGYAILKCNNKTFNGTGPCNNV
STVQCTHGIKPVVSTQLLLNGSLAEGEIIIRSENLTNNVKTIIVHLNES
VEIVCTRPNNNTRKSIRIGPGQTFYATGDIIGNIRQAYCNIKKDDWIRT
LQRVGKKLAEHFPRRIINFTSPAGGDLEITTHSFNCRGEFFYCNTSSLF
NSTYNPNDTNSNSSSSNSSLDITIPCRIKQIINMWQEVGRAMYAPPIEG
NITCKSNITGLLLVRDGGVESNETEIFRPGGGDMRNNWRSELYKYKVVE
IKPLGIAPTAAKRRVVEREKRGSAGSAGSSRSAGSAGSAGSEMVLENVT
ENFNMWKNDMVEQMHEDVISLWDQSLKPCVKLTPLCVTLECRQVNTTNA
TSAAA or variant thereof, 16055-CycP (clade C).

In certain embodiments, the chimeric proteins comprises an amino acid sequence (SEQ ID NO: 4)
EEDPCACESLVKFQAKVEGLLQALTRKLEAVSKRLAILENTVVASSVNV
TNGEVMKNCSFNATTELKDKKHKVHALFYKLDVVPLNGNSSSSGEYRLI
NCNTSAITQACPKVSFDPIPLHYCAPAGFAILKCNNKTFNGTGPCRNVS -continued

```
TVQCTHGIKPVVSTQLLLNGSLAEEEIIRSENLTNNAKTIIVHLNESV

NINCTRPNNNTRKSIRIGPGQTFYATGDIIGNIRQAHCNINESKWNNTL

QKVGEELAKHFPSKTIKFEPSSGGDLEITTHSFNCRGEFFYCNTSDLFN

GTYRNGTYNHTGRSSNGTITLQCKIKQIINMWQEVGRAIYAPPIEGEIT

CNSNITGLLLLRDGGQSNETNDTETFRPGGGDMRDNWRSELYKYKVVEI

KPLGVAPTEAKRRVVEREKRGSAGSAGSSRSAGSAGSAGSEMVLANVTE

NFNMWKNDMVEQMHEDIISLWDESLKPCVKLTPLCVTLNCTNVKGNESD

TAAA or variant thereof, 1086C-CycP (clade C).
```

In certain embodiments, the chimeric proteins comprises an amino acid sequence

```
                                              (SEQ ID NO: 5)
EEDPCACESLVKFQAKVEGLLQALTRKLEAVSKRLAILENTVVASSVNV

TNGEEIKNCSFNTTTEIRDKKQKEYALFYRLDIVPLNEERKGNSSEYRL

INCNTSTITQACPKVSFDPIPIHYCAPAGYAILKCNNKTFNGTGPCNNV

STVQCTHGIKPVVSTQLLLNGSLAEEEIIRSENLTNNAKTIIVHLNES

VEINCTRPNNNTRKSIRIGPGQTFYATGDIIGDIRQAHCNISESKWNKT

LQRVSKKLKEHFPNKTIKFAPSSGGDLEITTHSFNCRGEFFYCNTSKLF

NSTYNNNTSNSTITLPCRIKQIINMWQEVGRAMYAPPIAGNITCKSNIT

GLLLTRDGGNNNNTTETFRPGGGDMRDNWRSELYKYKVVEIKPLGIAPT

KAKRRVVEREKRGSAGSAGSSRSAGSAGSAGSEMVLENVTENFNMWKND

MVDQMHEDTTSLWDQSLKPCVKLTPLCVTLNCTNVNVTNATSAAA or variant thereof, Consensus C-CycP (clade C).
```

In certain embodiments, the N-terminus of the chimeric proteins consist of the trimerization domain.

In certain embodiments, trimerization domain comprises EEDPCACESLVKFQAKVEGLLQALTRKLEAVSKR-LAILENTVV (SEQ ID NO: 6) or variant thereof.

In certain embodiments, the first segment of HIV variable domain 1 comprises an amino acid sequence $X^1X^2CX^3X^4X^5X^6C$ wherein $X^1$ is P or any amino acid, $X^2$ is L or any amino acid, $X^3$ is V or any amino acid, $X^4$ is T, S, or any amino acid, $X^5$ is L or any amino acid, and $X^6$ is D, E, N, T, H, K, or any amino acid.

In certain embodiments, the first segment of HIV variable domain 1 comprises an amino acid sequence PLCVTLNC (SEQ ID NO: 8).

In certain embodiments, the second segment of HIV variable domain 1 comprises an amino acid sequence $X^1X^2X^3X^4MX^5X^6$ wherein $X^1$ is N, S, T or any amino acid, $X^2$ is E, A, D, G, K, or any amino acid, $X^3$ is N, S, G, M, T or any amino acid, $X^4$ is M, S, or any amino acid, $X^5$ is E, K, T, or any amino acid, and $X^6$ is H, M, R or any amino acid.

In certain embodiments, the second segment of HIV variable domain 1 comprises an amino acid sequence SEGTMER (SEQ ID NO: 10).

In certain embodiments, the HIV variable domain 2 comprises an amino acid sequence $X^1CX^2X^3X^4X^5X^6$ wherein $X^1$ is N or any amino acid, $X^2$ is S or any amino acid, $X^3$ is F, Y, or any amino acid, $X^4$ is N or any amino acid, $X^5$ is I, A, L, Y or any amino acid, and $X^6$ is T or any amino acid.

In certain embodiments, the HIV variable domain 2 comprises an amino acid sequence NCSFNIT (SEQ ID NO: 12)

In certain embodiments, the HIV variable domain 2 comprises an amino acid sequence $X^1DX^2X^3X^4X^5X^6$ wherein $X^1$ is R, K, or any amino acid, $X^2$ is E, R, K, or any amino acid, $X^3$ is K, V, E, or any amino acid, $X^4$ is H, Q, K, or any amino acid, $X^5$ is K, N, or any amino acid, and $X^6$ is E, V, or any amino acid.

In certain embodiments, the HIV variable domain 2 comprises an amino acid sequence RDEVQKE (SEQ ID NO: 14) or KDKKHKV (SEQ ID NO: 15).

In certain embodiments, the HIV variable domain 3 comprises an amino acid sequence $X^1IX^2X^3X^4X^5X^6$ (SEQ ID NO: 16) wherein $X^1$ is R, H, P, or any amino acid, $X^2$ is G or any amino acid, $X^3$ is P or any amino acid, $X^4$ is G or any amino acid, $X^5$ is Q, R, or any amino acid, and $X^6$ is T, A, or any amino acid.

In certain embodiments, the HIV variable domain 3 comprises an amino acid sequence HIGPGRA (SEQ ID NO: 17).

In certain embodiments, the HIV variable domain 3 comprises an amino acid sequence $X^1X^2X^3DX^4X^5X^6$ wherein $X^1$ is I or any amino acid, $X^2$ is I, T, or any amino acid, $X^3$ is G or any amino acid, $X^4$ is I or any amino acid, $X^5$ is R, or any amino acid, and $X^6$ is Q, K, or any amino acid.

In certain embodiments, the HIV variable domain 3 comprises an amino acid sequence IIGDIRQ (SEQ ID NO: 19).

In certain embodiments, the N-terminus of the chimeric proteins consist of the trimerization domain.

In certain embodiments, the trimeric protein complexes contain a chimeric protein disclosed herein, e.g., SEQ ID NO: 1, 2, 3, 4, 5, variant, or combination thereof. In certain embodiments, the combination of trimeric protein complex includes sequences associated with clades A, B, C, D, F, G, H, J, and combinations thereof. In certain embodiments, the combination of trimeric protein complex includes sequences associated with clade A, clade B, and clade C. In certain embodiments, the combination includes sequences associated with clade A and clade B. In certain embodiments, the combination includes sequences associated with clade B and clade C. In certain embodiments, the combination includes sequences associated with clade A and clade C.

In certain embodiments, the combination of trimeric protein complex includes sequences associated with SEQ ID NO: 1, 2, and 3. In certain embodiments, the combination of trimeric protein complex includes sequences associated with SEQ ID NO: 1, 2, and 4. In certain embodiments, the combination of trimeric protein complex includes sequences associated with SEQ ID NO: 1, 2, and 5.

In certain embodiments, the variant has greater than 20% identity or similarity to a sequence disclose herein such as SEQ ID NO: 1, 2, 3, 4, 5. In certain embodiments, the variant has greater than 25% identity or similarity to a sequence disclose herein such as SEQ ID NO: 1, 2, 3, 4, 5. In certain embodiments, the variant has greater than 30% identity or similarity to a sequence disclose herein such as SEQ ID NO: 1, 2, 3, 4, 5. In certain embodiments, the variant has greater than 35% identity or similarity to a sequence disclose herein such as SEQ ID NO: 1, 2, 3, 4, 5. In certain embodiments, the variant has greater than 40% identity or similarity to a sequence disclose herein such as SEQ ID NO: 1, 2, 3, 4, 5. In certain embodiments, the variant has greater than 45% identity or similarity to a sequence disclose herein such as SEQ ID NO: 1, 2, 3, 4, 5. In certain embodiments, the variant has greater than 50% identity or similarity to a sequence disclose herein such as SEQ ID NO: 1, 2, 3, 4, 5. In certain embodiments, the variant has greater than 55% identity or similarity to a sequence disclose herein such as SEQ ID NO: 1, 2, 3, 4, 5. In certain embodiments, the variant has greater than 60% identity or similarity to a sequence disclose herein such as SEQ ID NO: 1, 2, 3, 4, 5. In certain embodiments, the variant has greater than 65% identity or similarity to a sequence disclose herein such as SEQ ID NO: 1, 2, 3, 4, 5. In certain embodiments, the variant has greater than 70% identity or similarity to a sequence disclose herein such as SEQ ID NO: 1, 2, 3, 4, 5. In certain embodiments, the variant has greater than 75% identity or similarity to a sequence disclose herein such as SEQ ID NO: 1, 2, 3, 4, 5. In certain embodiments, the variant has greater than 80% identity or similarity to a sequence disclose herein such as SEQ ID NO: 1, 2, 3, 4, 5. In certain embodiments, the variant has greater than 85% identity or similarity to a sequence disclose herein such as SEQ ID NO: 1, 2, 3, 4, 5. In certain embodiments, the variant has greater than 90% identity or similarity to a sequence disclose herein such as SEQ ID NO: 1, 2, 3, 4, 5. In certain embodiments, the variant has greater than 95% identity or similarity to a sequence disclose herein such as SEQ ID NO: 1, 2, 3, 4, 5. In certain embodiments, the variant has greater than 98% identity or similarity to a sequence disclose herein such as SEQ ID NO: 1, 2, 3, 4, 5.

With specific regard to trimeric cyclically permuted gp120 that contain chimeric protein disclosed herein, any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

For example, non-conservative substitutions may involve the exchange of a member of one of these classes for a member from another class. In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157: 105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological uses. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0+1); glutamate (+3.0+1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Human Immunodeficiency Virus (HIV)

According to a preferred embodiment of the present disclosure, recombinant viral vectors encode and express an HIV env. The etiological agent of acquired immune deficiency syndrome (AIDS) is recognized to be a retrovirus exhibiting characteristics typical of the lentivirus genus, referred to as human immunodeficiency virus (HIV). HIV-2 is more closely related to a virus isolated from sooty mangabey monkeys in the wild, than to HIV-1. It is currently believed that HIV-2 represents a zoonotic transmission of SIV to man. A series of lentiviral isolates from captive chimpanzees are close genetic relatives of HIV-1.

Distinct genetic subtypes or clades of HIV-1 are defined and classified into three groups: M (major); O (outlier); and N (non-M or O). The M group of HIV-1, which includes over 95% of the global virus isolates, consists of at least eight discrete clades (A, B, C, D, F, G, H, and J), based on the sequence of complete viral genomes. HIV-1 genetic variation comes from studies of group M viruses of diverse geographic origin. The HIV-1 population present within an infected individual can vary from 6% to 10% in nucleotide sequence. HIV-1 isolates within a clade may exhibit nucleotide distances of 15% in gag and up to 30% in gp120 coding sequences. Interclade genetic variation may range between 30% and 40% depending on the gene analyzed.

Isolates can also be grouped on the basis of chemokine receptor utilization in fusion assays in which HIV-1 gp120 and CD4+ coreceptor proteins are expressed in separate cells. HIV-1 isolates using the CXCR4 receptor (now designated X4 viruses) are usually T cell line (TCL)-tropic syncytium inducing (SI) strains, whereas those exclusively utilizing the CCR5 receptor (R5 viruses) are predominantly macrophage (M)-tropic and non-syncytium inducing (NSI). The dual-tropic R5/X4 strains, which may comprise the majority of patient isolates and exhibit a continuum of tropic phenotypes, are frequently SI.

The three primary HIV-1 translation products are initially synthesized as polyprotein precursors, which are subsequently processed by viral or cellular proteases into mature particle-associated proteins. The 55-kd Gag precursor is cleaved into the matrix (MA), capsid (CA), nucleocapsid (NC), and p6 proteins. Autocatalysis of the 160-kd Gag-Pol polyprotein, Gag-Pol, gives rise to the protease (PR), the heterodimeric reverse transcriptase (RT), and the integrase (IN) proteins, whereas proteolytic digestion by a cellular enzyme(s) converts the glycosylated 160-kd Env precursor gp160 to the gp120 surface (SU) and gp41 transmembrane (TM) cleavage products. The remaining six HIV-1-encoded proteins (Vif, Vpr, Tat, Rev, Vpu, and Nef) are the primary translation products of spliced mRNAs.

The HIV Env glycoproteins play a major role in the virus life cycle. They contain the determinants that interact with the CD4 receptor and coreceptor, and they catalyze the fusion reaction between the lipid bilayer of the viral envelope and the host cell plasma membrane. In addition, the HIV Env glycoproteins contain epitopes that elicit immune responses that are important from both diagnostic and vaccine development perspectives.

The HIV Env glycoprotein is synthesized from the singly spliced 43-kb Vpu/Env bicistronic mRNA; translation occurs in ribosomes associated with the rough endoplasmic reticulum (ER). The 160-kd polyprotein precursor (gp160) is an integral membrane protein that is anchored to cell membranes by a hydrophobic stop-transfer signal in the domain destined to be the mature TM Env glycoprotein, gp41. The gp160 is co-translationally glycosylated, forms disulfide bonds, and undergoes oligomerization in the ER. The predominant oligomeric form appears to be a trimer, although dimers and tetramers are also observed. The gp160 is transported to the Golgi, where it is proteolytically cleaved by cellular enzymes to the mature SU glycoprotein gp120 and TM glycoprotein gp41. Subsequent to gp160 cleavage, gp120 and gp41 form a noncovalent association that is critical for transport of the Env complex from the Golgi to the cell surface.

The HIV Env glycoprotein complex, in particular the SU (gp120) domain, is very heavily glycosylated; approximately half the molecular mass of gp160 is composed of oligosaccharide side chains. During transport of Env from its site of synthesis in the ER to the plasma membrane, many of the side chains are modified by the addition of complex sugars. The numerous oligosaccharide side chains form what could be imagined as a sugar cloud obscuring much of gp120 from host immune recognition. SU, gp120, contains interspersed conserved (C1 to C5) and variable (V1 to V5) domains. The Cys residues present in the gp120s of different isolates are highly conserved and form disulfide bonds that link the first four variable regions in large loops.

In the steps leading to membrane fusion CD4 binding induces conformation changes in Env that facilitate coreceptor binding. Following the formation of a ternary gp120/CD4/coreceptor complex, gp41 adopts a hypothetical conformation that allows the fusion peptide to insert into the target lipid bilayer. The formation of the gp41 six-helix bundle (which involves antiparallel interactions between the gp41 N- and C-helices) brings the viral and cellular membranes together and membrane fusion takes place.

Recombinant Nuclei Acids and Viral Vectors

In certain embodiments, the disclosure relates to recombinant viral vectors, recombinant vectors, and recombinant plasmids comprising nucleic acids encoding chimeric proteins disclosed herein. In certain embodiments, this disclosure relates to expression systems comprising nucleic acids and vectors disclosed herein.

Nucleic acids, vectors, and expression constructs can be introduced in vivo via lipofection (DNA transfection via liposomes prepared from synthetic cationic lipids). Synthetic cationic lipids can be used to prepare liposomes to encapsulate a nucleic acid, vector, or expression construct of the disclosure. A nucleic acid, vector, or expression construct can also be introduced as naked DNA or RNA using methods known in the art, such as transfection, microinjection, electroporation, calcium phosphate precipitation, and by biolistic methods.

If a recombinant virus vector of this disclosure is constructed starting with a vaccinia virus, the majority of the nucleic acid molecules and proteins in the recombinant virus vector will come from vaccinia virus and thus the final recombinant virus vector can be referred to, for example, as a recombinant vaccinia virus vector or a vaccinia-based recombinant virus vector. In certain embodiments, the recombinant virus vector is selected from the group consisting of a recombinant poxvirus vector, a recombinant vaccinia virus vector, a recombinant chordopoxvirus vector, a recombinant iridovirus vector, a recombinant adenovirus vector, a recombinant adeno-associated virus vector, a recombinant SV40 virus vector, a recombinant Epstein-Barr virus vector, a recombinant herpes virus vector and a recombinant JC virus vector.

In certain embodiments, this disclosure contemplates that methods disclosed herein are used with recombinant virus, preferably recombinant MVA viruses. MVA is an attenuated strain of vaccinia virus originally developed as a vaccine for smallpox. The ability of MVA to infect mammalian, including human host cells, is restricted due to known deletions in the virus genome. In addition to the safe use in human vaccinations, Wyatt et al. report mice with severe combined immunodeficiency disease remained healthy when inoculated with MVA. Proc Natl Acad Sci USA. 2004, 101(13): 4590-5. MVA can be engineered in deleted regions to express heterologous genes to induce protective immunity to other viruses. Sutter et al. report a recombinant MVA stimulated protective immunity in mice to influenza virus. Vaccine, 1994, 12(11):1032-40.

A recombinant MVA/HIV construct, named MVA/HIV 48, is reported in Wyatt et al. AIDS Res Hum Retroviruses. 2004, 20(6):645-53. Flanking deletion III of the MVA genome, MVA/HIV 48 contains chimeric HIV-1 HXB-2/BH10 gag-pol sequences, a deletion of integrase, inactivating point mutations in reverse transcriptase, and HIV-1 ADA env sequences with a truncation of most of the cytoplasmic domain. Chimeric HIV-1 HXB-2/BH10 gag-pol contains the HXB2 gag which replace first 1872 nucleotides of the HIV strain BH10 gag-pol. Env from HIV clade B strain ADA is truncated by a deletion of 115 amino acids of the cytoplasmic tail of gp41 yielding a terminal sequence of GGDRD (SEQ ID NO: 16). Expression in cells results in virus-like particles containing Env. See also U.S. Pat. Nos. 5,849,304; 8,916,172; and 9,133,480.

Additional, double recombinant MVA/HIV constructs have been produces by inserting a chimeric HXB-2/BH10 gag-pol sequences into the deletion III of MVA and inserting HIV env gene into the deletion II of MVA. See Wyatt et al. Vaccine, 2008, 26(4): 486-493. Double recombinant viruses with env genes inserted in deletion II of MVA were named MVA62B and MVA62BSm, respectively, based on insertion at either NotI or SmaI restriction sites in a starting plasmid (pLAS-2). Two independent clones of MVA62BSm and MVA62BSp, designated 1 and 2, were isolated.

Combined DNA and recombinant modified vaccinia Ankara (MVA62B) vaccines can produce virus-like particles that display membrane-bound trimeric forms of Env. The DNA components are reported to expresses Gag, protease, reverse transcriptase, Tat, Rev, and Vpu from clade B HIV-HXB-2/BH10 chimeric sequences and Env from HIV ADA sequences. See Smith et al. DNA/MVA vaccine for HIV type 1: effects of codon-optimization and the expression of aggregates or virus-like particles on the immunogenicity of the DNA prime. AIDS Res Hum Retroviruses, 2004, 20:1335-47.

As a result of extensive passage in cell culture, the MVA virus genome contains six major deletions, referred to as Del I, II, II, IV, V and VI. Historically, the region around Del II and Del III has been used for insertion of heterologous nucleic acid sequences.

As used herein, the term heterologous is a comparative term, and refers to a molecule that is from an organism different from that to which it is being referenced or that is made synthetically. The molecule can be a protein or a nucleic acid sequence (i.e., RNA or DNA). For example, a heterologous nucleic acid sequence in a recombinant virus vector refers to the fact that the heterologous nucleic acid sequence is or may be from an organism other than the base virus used to construct the recombinant virus vector. As a further example, a heterologous nucleic acid sequence in a recombinant vaccinia virus vector refers to the fact that the heterologous nucleic acid sequence is from an organism other than vaccinia virus or that was made synthetically.

A heterologous nucleic acid sequence can be inserted at any location in a recombinant virus vector genome, as long as such insertion does not unintentionally alter the functioning of the resulting recombinant virus vector. For example, a nucleic acid sequence can be inserted into a non-essential region. Such non-essential regions include, but are not limited to, naturally occurring deletions within the viral genome (e.g., Del I, II, II, etc. of modified vaccinia virus Ankara (MVA), intergenic regions or non-essential genes. A non-essential region is a genomic region, the alteration of which has no, or almost no, discernible effect on viral replication and the production of progeny virus. One example of a non-essential region is a non-essential gene such as, for example, the vaccinia virus hemagglutinin gene.

Alternatively, a nucleic acid sequences can be inserted into an essential region of the genome (e.g., an essential gene). It will be appreciated that interruption of an essential region will result in a recombinant virus vector unable to complete the virus life cycle and produce progeny virus. However, such recombinant virus vectors can produce progeny virus when grown in cells that provide the missing function. Such a cell can be referred to as a complementing cell because it provides the function usually provided by the essential gene. That is, it "complements" the recombinant virus vector. Conversely, a cell that is unable to provide the missing viral function can be referred to as a non-commenting cell. Such culture systems are disclosed herein. At least one heterologous nucleic acid sequence may be inserted into the gene required for expression of post-replicative viral genes.

Pharmaceutical Compositions

The present disclosure also provides pharmaceutical compositions and vaccines for inducing a protective immune response in a living animal body, including a human. In certain embodiments, the pharmaceutical compositions comprise trimeric cyclically permuted gp120 that contain chimeric protein disclosed herein or nucleic acid encoding the same. The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like.

In certain embodiments, the disclosure relates to pharmaceutical compositions comprising trimeric protein complex or combination of trimeric protein complexes comprising chimeric proteins disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the trimeric protein complex or combination of trimeric protein complexes comprising chimeric proteins disclosed herein may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the trimeric protein complex or combination of trimeric protein complexes comprising chimeric proteins disclosed herein, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

In certain embodiments, production processes are contemplated which two components, trimeric protein complex or combination of trimeric protein complexes comprising chimeric proteins disclosed herein and a pharmaceutical carrier, are provided already in a combined dry form ready to be reconstituted together. In other embodiments, it is contemplated that a trimeric protein complex or combination of trimeric protein complexes comprising chimeric proteins disclosed herein, and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe, vial, or other housing for administering the reconstituted pharmaceutical composition after contact with the diluent. In certain embodiments, the coated compounds can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as syringes, vials, tubes, etc. The pharmaceutical composition may then preferably be applied via specific needles of the syringe, nozzle, or via suitable catheters. A typical diluent comprises water for injection, and NaCl (preferably 50 to 150 mM, especially 110 mM), $CaCl_2$) (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

Figure 1C:
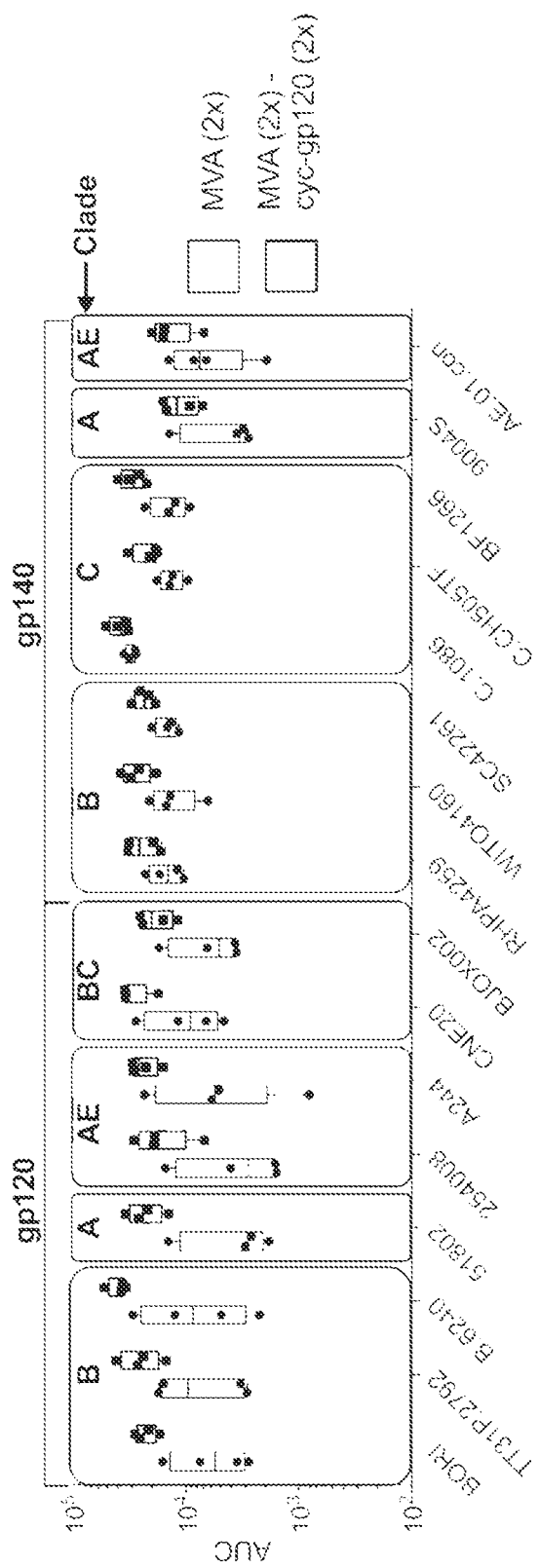
FIG. 1C shows BAMA analysis of sera from weeks 10 and 34 against gp120/gp140 proteins reported as AUC analysis values. Shaded area represents threshold for positive reactivity.
Figure 1D:
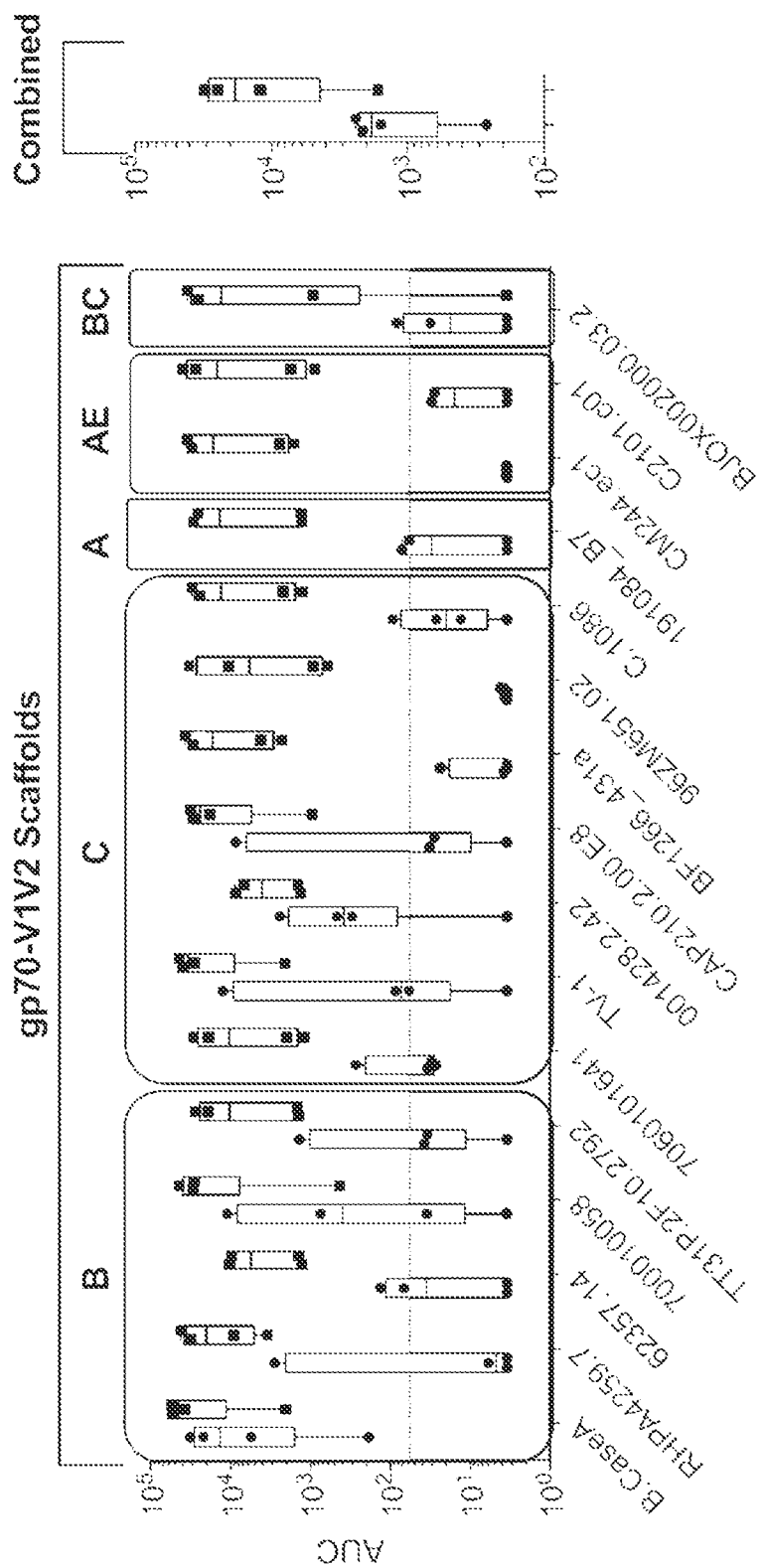
FIG. 1D shows data against gp70-V1V2 scaffold proteins.
Figures 1E, 2A:
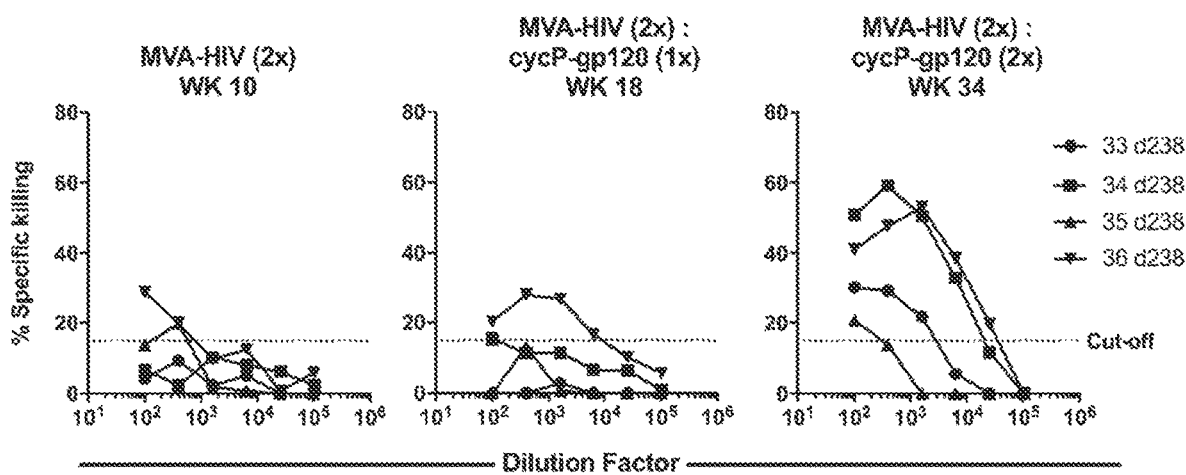
FIG. 1E shows data on V2 hot-spot binding, detected by ELISA, from week 10 and week 34 sera.
FIG. 2A shows on ADCC activity week 10 from rabbits immunized with cycP-gp120 alone.

For the preparation of vaccines, a recombinant virus or plasmid is typically converted into a physiologically acceptable form. This can be done based on the experience in the preparation of poxvirus vaccines used for vaccination against smallpox. For example, the purified virus is stored at −80° C. with a titer of $5 \times 10^8$ TCID 50/ml formulated in about 10 mM Tris, 140 mM NaCl pH 7.4. For the preparation of vaccine shots, e.g., $10^2$-$10^8$ particles of the virus are lyophilized in 100 ml of phosphate buffered saline (PBS) in the presence of 2% peptone and 1% human albumin in an ampoule, preferably a glass ampoule. Alternatively, the vaccine shots can be produced by stepwise freeze-drying of the recombinant virus in a formulation. This formulation can contain additional additives such as mannitol, dextran, sugar, glycine, lactose or polyvinylpyrrolidone or other aids such as antioxidants or inert gas, stabilizers or recombinant proteins (e.g., human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy the lyophilisate can be dissolved in 0.1 to 0.5 ml of an aqueous solution, preferably physiological saline or Tris buffer, and administered either systemically or locally, i.e., parenterally, subcutaneous, intramuscularly, by scarification or any other path of administration know to the skilled practitioner.

In certain embodiments, this disclosure contemplates a kit comprising pharmaceutical compositions disclosed herein and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles, nozzles, or catheters, extra vials or further wound covering means. In certain embodiments, the kit comprises a syringe housing the dry and stable hemostatic composition and a housing or syringe containing the diluent (or provided to take up the diluent from another diluent container).

EXAMPLES

Trimeric Cyclically Permuted Gp120 (cycP-Gp120) Serves as a Strong Booster Immunization in Rabbits Primed with MVA-HIV The immunogenicity of cycPgp120 was tested in a protein prime/boost approach in rabbits and as a booster immunization to DNA/modified vaccinia Ankara (MVA)-vaccinated rabbits and rhesus macaques. In rabbits, two cycP-gp120 protein immunizations induced 100-fold higher titers of high-avidity gp120-specific IgG than two gp120 immunizations, with four total gp120 immunizations being required to induce comparable titers. cycP-gp120 also induced markedly enhanced neutralizing activity against tier-1A and -1B HIV-1 isolates, substantially higher binding and breadth to gp70-V1V2 scaffolds derived from a multiclade panel of global HIV-1 isolates, and antibodies targeting key regions of the V2-loop region associated with reduced risk of infection in RV144. Similarly, boosting MVA- or DNA/MVA-primed rabbits or rhesus macaques with cycP-gp120 showed a robust expansion of gp70-V1V2-specific IgG, neutralization breadth to tier-1B HIV-1 isolates, and antibody-dependent cellular cytotoxicity activity. These results demonstrate that cycP-gp120 serves as a robust HIV Env immunogen that induces broad anti-V1V2 antibodies and promotes neutralization breadth against HIV-1.

The ability of cycP-gp120 to boost humoral immune responses primed by another recombinant poxvirus was evaluated. Modified vaccinia Ankara (MVA) engineered to express trimeric membrane-bound gp150 derived from HIV-1 clade B strain ADA (MVA-HIV) on infected cells and virus-like particles. Rabbits were immunized with MVA-HIV (MVA-62BSm) and cycP-gp120 in a poxvirus prime/protein boost scheme. New Zealand White rabbits (age, 10 to 12 weeks) were immunized intramuscularly with 20 μg of recombinant JRFL-gp120 (weeks 0, 8, 16, and 32) or JRFL-hCMP-V1cyc-gp120 (cycP-gp120) (weeks 0 and 8). Both JRFL-gp120 and cycP-gp120 contain the E168K mutation. An additional group was immunized intramuscularly with $1\times10^8$ PFU MVA-62BSm (weeks 0 and 8), followed by boosting with cycP-gp120 (weeks 16 and 32). JRFL-gp120 and cycP-gp120 immunizations were given with the adjuvant Adjuplex™ (Sigma).

Two MVA-HIV immunizations induced strong binding antibodies against JRFL-gp120 (mean titer, 5.1 logs), and these responses were boosted by approximately 1 log upon subsequent immunization with cycP-gp120 before contracting over the next 14 weeks before a final cycP-gp120 boost (mean titer, 5.7 logs) (FIG. 1A). Neutralizing antibody responses were measured at week 10, after the second MVA-HIV immunization, week 18, after the first cycP-gp120 boost, and week 34, after the final cycP-gp120 boost. Encouragingly, boosting once with cycP-gp120 expanded both tier-1A and -1B neutralizing antibodies (FIG. 1). However, the second protein boost did not efficiently recall the antibody response, and thus the neutralizing antibody titers also were not boosted following the second protein boost (FIG. 1). Analysis at week 34, 2 weeks after the second cycP-gp120 immunization, showed an expansion of binding to the global panel of HIV-1 gp120/gp140 proteins, highlighting the ability of cycP-gp120 to promote and expand antibodies with multiclade breadth (FIG. 1C). While MVA-HIV immunization induced strong gp120 binding antibodies, responses against gp70-V1V2 scaffolds were much weaker, with only 1 out of 16 isolates tested, Case.A2, showing 100% positive binding in MVA-HIV-immunized animals. However, boosting with two cycP-gp120s greatly expanded both the magnitude and breadth of gp70-V1V2-directed responses, with 15 out of 16 isolates showing positive binding by all animals (FIG. 1D), demonstrating cycPgp120's propensity for inducing V1V2-directed antibody responses. As with rabbits immunized only with cycP-gp120, boosting MVA-primed rabbits with cycP-gp120 also promoted the generation of V2 hot-spot binding antibodies, responses not observed after the initial MVA-HIV immunizations (FIG. 1E). These data show that cycP-gp120 acts as a strong boosting immunogen in MVA-HIV-primed animals, promoting both V1V2-scaffold- and V2 hot-spot-directed responses.

A major effector function of non-neutralizing antibody responses is antibody dependent cellular cytotoxicity (ADCC), and recent studies examining antibody responses from the RV144 trial suggest that ADCC is involved with vaccine efficacy. To measure ADCC activity in rabbits, HIV-1 JRFL-infected target cells were cocultured with effector NK cells and serial dilutions of rabbit sera taken at different time points. While MVA-HIV immunization led to a low level of ADCC activity, this activity was boosted after the two cycP-gp120 boosts (FIG. 2A), with all four rabbits developing ADCC activity against HIV-1-infected cells. In contrast, immunization with cycP-gp120 alone resulted in only one animal out of four developing ADCC activity (FIG. 2B), despite having similar if not higher levels of anti-JRFL gp120 serum IgG titers than MVA-HIV-primed, cycPgp120-boosted rabbits (FIGS. 2C and D). Additionally, both groups have strong V1V2-directed breadth and JRFL-gp120 V2 hot-spot-directed antibodies. While the difference in ADCC titers in animals immunized with cycP-gp120 or MVA-HIV prime/cycP-gp120 boost does not reach statistical significance, these data suggest that the development of ADCC activity is not based solely on the magnitude or specificity of the antibody response. Additionally, these data suggest that the utilization of a poxvirus vector prime prior to a protein boost could aid in the development of ADCC functionality.

cycP-Gp120 Serves as a Strong Booster Immunization to MVA-Primed Antibody Responses in Rhesus Macaques.

Figure 3A:
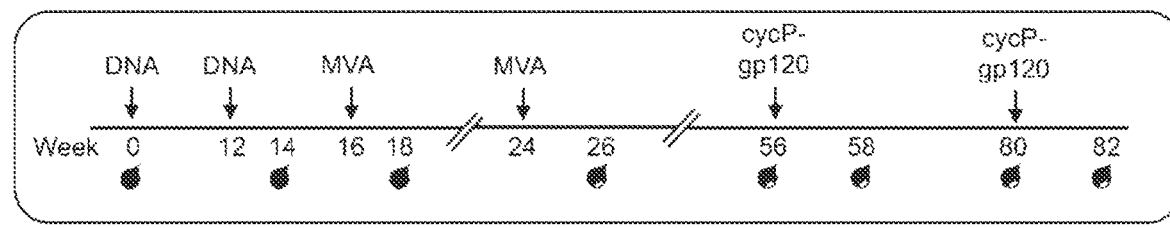
FIG. 3A shows a study design for boosting rhesus macaques primed with a DNA/MVA vaccine with cycP-gp120. Four rhesus macaques were immunized with DNA expressing HIV-1 gag/pol/env at weeks 0 and 12 and boosted with MVA-HIV at weeks 16 and 24 before boosting with recombinant JRCSF cycP-gp120 protein at weeks 56 and 80.

To test the immunogenicity of cycP-gp120 in the nonhuman primate model, four rhesus macaques were intramuscularly vaccinated with a clade B DNA/MVA HIV vaccine, followed by two subcutaneous boosts with HIV-1 JRCSF cycP-gp120 (FIG. 3A). Four Indian rhesus macaques were immunized intramuscularly with two DNA primes (weeks 0 and 12) followed by two MVA-62Bsm boosts (weeks 16 and 24), with both vaccines encoding HIV-1 clade B HxB2 gag/pol and ADA env. In addition, animals were boosted subcutaneously with 100 µg of JRCSF-cycP-gp120 with Adjuplex™ at weeks 56 and 58.

Figure 3B:
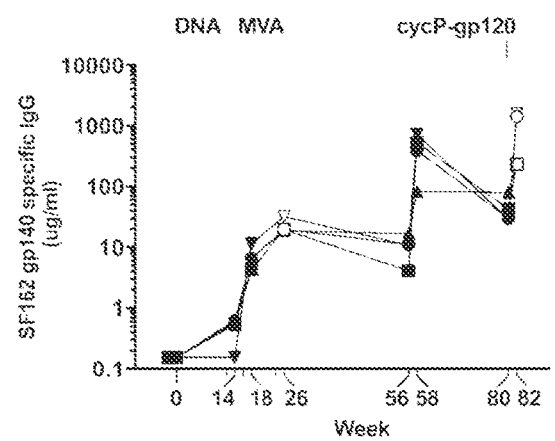
FIG. 3B shows kinetic analysis of serum IgG specific for HIV-1 SF162 gp140 (µg/ml).
Figure 3C:
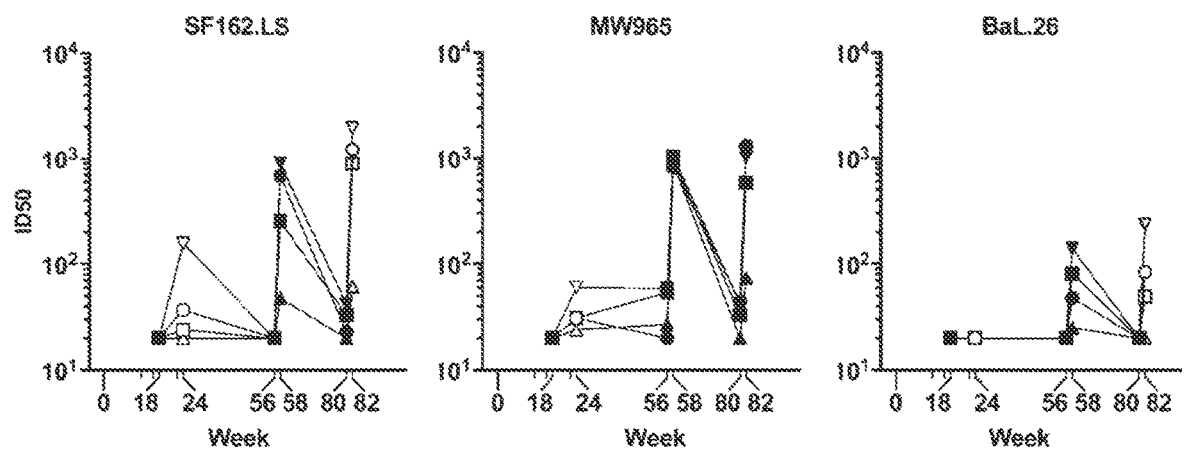
FIG. 3C shows data on neutralizing antibodies against tier-1A (SF162.LS and MW965) and -1B (BaL.26).
Figure 3D:
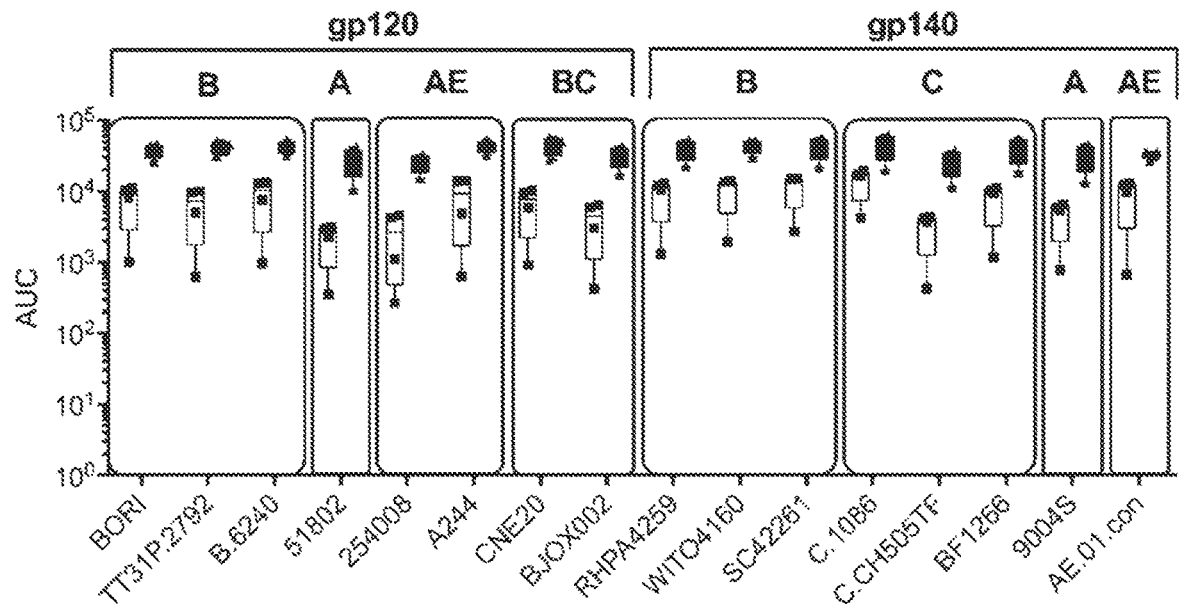
FIG. 3D shows BAMA analysis of week 26 and week 82 sera against a global panel of HIV-1 gp120, gp140, reported as AUC values.
Figure 3E:
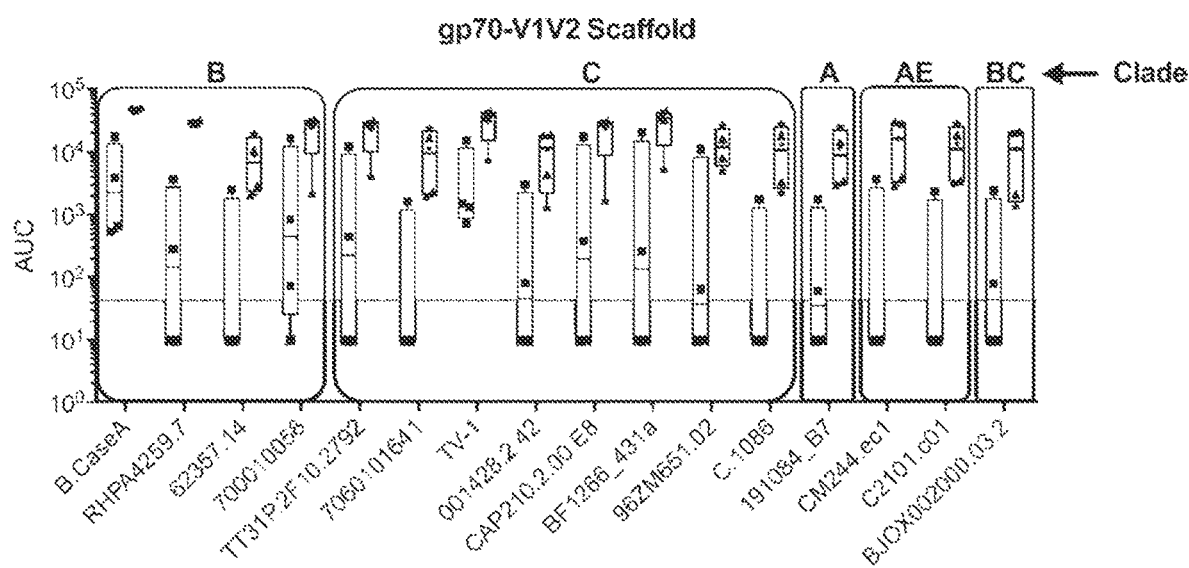
FIG. 3E shows data on gp70-V1V2 scaffold proteins.

In rhesus macaques cycP-gp120 served as a potent immunogen, boosting both gp140-specific serum IgG as well as neutralizing antibodies against tier-1A and -1B HIV-1 isolates, with neutralizing antibodies against the moderately resistant HIV-1 BaL.26 being detected only after boosting with cycPgp120 (FIGS. 3B and C). Boosting with cycP-gp120 enhanced the magnitude of cross-reactive antibodies specific for gp120 and gp140 antigens and greatly expanded the global gp70-V1V2 response, with all animals reacting against all scaffolds tested after the second protein boost (FIGS. 2D and E). Taken together, these data show that cycP-gp120 can serve as a potent vaccine immunogen in rhesus macaques.

Vaccination to the Sublingual and Buccal Tissue (SL/B) Mucosa

Female rhesus macaques were immunized orally via either topical application to the SL/B tissue, needle-free pressure injection to the SL/B tissue, or the conventional intradermal and subcutaneous route (ID/SC). Macaques were immunized twice with $1 \times 10^8$ pfu of MVA-HIV expressing HIV-1 clade B gag, pol, env (strain ADA) followed by two boosts with 100 ug of trimeric clade B cycP-gp120 immunogen (strain JRFL) along with the mucosal adjuvant dmLT. The adjuvant dmLT, or LT(R192G/L211A), is a detoxified version of the heat-labile enterotoxin of *Escherichia coli* with two mutations in its A-subunit that remove the enterotoxicity but preserve the adjuvanticity of the molecule. See Norton et al. Clin Vaccine Immunol, 18 (2011), pp. 546-551. Doses were split in half between the sublingual and buccal tissue or the left and right thigh of ID/SC immunization.

MVA-HIV expresses trimeric HIV-1 envelope (gp150) on the surface of infected cells and produces virus like particles (VLPs). CycPgp120 is a trimeric gp120 immunogen, stabilized by a heterologous trimerization domain inserted into the V1-loop of a cyclic permutated gp120. Needle-free SL/B and topical SL/B cycP-gp120 immunization were adjuvanted with 25 ug of dmLT per site, while subcutaneous cycP-gp120 immunization in the ID/SC group was adjuvanted with 1 ug of dmLT. Swelling of mouth was observed following the first cycP-gp120+dmLT boost. To make the second boost comparable between needle-free SL/B and ID/SC immunization, the dose of dmLT was reduced for the second cycP-gp120 immunization to 1 ug per site.

SL/B HIV-1 Immunization Induces Strong Systemic IgG Antibody Responses

Pressurized needle-free SL/B immunization generated a strong anti-ADA gp120 IgG response in serum, a feature that is not common for oral immunizations. Two MVA-HIV immunizations induced low levels of binding antibodies (geo-mean titer, 9.6 ug/ml) that were boosted remarkably by 100-fold following the 1st protein boost (geo-mean titer, 1012 ug/ml). These responses contracted by 10-fold over 8 weeks and were marginally boosted upon the $2^{nd}$ protein boost (geo-mean titer, 258 ug/ml). At the time of pre-challenge, 14 weeks after the final protein boost, anti-gp120 serum IgG titers had contracted about 10-fold (geo-mean titer, 27 ug/ml). In contrast, topical SL/B immunization resulted in minimal or undetectable antibody responses following both MVA-HIV and cycP-gp120 immunizations. Remarkably, while gp120-specific IgG responses induced by the needle-free SL/B immunization were comparable with ID/SC group following MVA immunizations, they were 10-fold (geo-mean titer 1012 vs. 120 ug/ml) and 3-fold higher (geo-mean titer, 258 vs 94 ug/ml) following the 1st and 2nd protein boosts, respectively. This may be because of the higher dose of the adjuvant used in the needle-free group during the 1st protein boost. Despite differences in the adjuvant doses, these data show that needle-free SL/B injection is an effective non-invasive method of generating high titers of vaccine specific serum IgG. DmLT is being investigated for its potential as a vaccine candidate against Enterotoxigenic *Escherichia coli* (ETEC) infection. Serum IgG responses were also measured against dmLT and found a strong anti-dmLT IgG response generated in needle-free SL/B immunized animals upon boosting with cycP-gp120 adjuvanted with dmLT. These results indicate that needle-free SL/B immunization is an effective route to non-invasively generate strong systemic vaccine-specific IgG antibody responses against multiple antigens.

SL/B Immunization Induces a Strong Mucosal IgG and IgA Response

As a major goal of mucosal vaccination is the generation of mucosal immune responses, vaccine-specific IgG and IgA antibodies were measured in the rectal, vaginal, and salivary secretions. Due to the variable amounts of immunoglobulin in secretions, antibody concentrations were normalized relative to the total IgG or IgA concentrations by calculating the specific activity (SA; ng gp120-specific IgG or IgA per total IgG or IgA). As with the systemic responses, needle-free SL/B immunization generated a strong gp120-specific IgG response in rectal, vaginal, and salivary secretions. Similar to serum IgG responses, the mucosal IgG responses also peaked after the 1st protein boost and the 2nd protein boost showed a small recall (<2-fold).

At the peak (wk25), the IgG SA was comparable between the three mucosal compartments (Geo-mean of specific activity; rectal, 56; vaginal 43; salivary, 51). Topical SL/B immunization generated minimal to undetectable mucosal antibodies, highlighting the importance of the needle-free injector to generate these responses. Additionally, while ID/SC immunization did result in mucosal IgG responses, these were significantly lower than needle-free SL/B responses at the peak time point (wk25). Mucosal IgG responses after the first protein boost contracted and were modestly expanded by the subsequent boost before contraction to the pre-challenge time point. Interestingly, while the gp120-specific rectal and vaginal IgG antibodies were maintained until pre-challenge, IgG antibodies in the saliva declined and approached undetectable levels, suggesting the establishment and maintenance of vaccine-specific IgG antibody responses varied between mucosal compartments.

Needle-free SL/B immunization also generated vaccine-specific IgA antibodies in all three mucosal compartments, with strongest responses in vaginal secretions with all animals generating detectable vaginal IgA responses (Geo-mean SA of 7.9) and weakest in saliva with only 2 out of 5 animals generating detectable IgA. The peak rectal and vaginal IgA response (wk25) was significantly higher in needle-free SL/B compared to ID/SC immunized animals, which generated minimal mucosal IgA responses, and these responses were largely undetectable in topical SL/B immunized animals. Rectal IgA and salivary IgA levels contracted over time and were predominately undetectable at the time of pre-challenge. However, vaginal IgA responses were still detectable at the time of pre-challenge, suggesting this route may generate durable vaginal antibody responses. In addition to gp120 specific antibodies, we also measured antibodies against the gp70-V1V2 scaffold antigen, which displays the variable loops 1-2 (V1V2) loops of gp120, as serum IgG antibodies directed against gp70-V1V2 were a major correlate of protection in the RV144 trial. Both needle-free SL/B and ID/SC immunization generated anti-gp70-V1V2 IgG in both rectal and vaginal secretions throughout the immunization regimen, however these responses were not long-lasting as they had contracted to undetectable levels by the pre-challenge time point. These results indicate that needle-free SL/B immunization is an easy and practical method of generating strong IgG responses in rectal, vaginal and oral mucosa, and strong IgA responses in vaginal mucosa.

Needle-Free SL/B Immunization Induces a Broadly Reactive HIV-1 Env IgG Response, Cross-Reactive V1V2 and V2 Hotspot Directed Antibodies, and Neutralizing Antibodies To address the global diversity of HIV-1, an effective vaccine should ideally recognize HIV-1 isolates from multiple strains and clades. To characterize the cross-reactivity of MVA/cycPgp120 induced antibodies, antibody binding was measured to a global panel of gp120, gp140 and gp70-V1V2 scaffold proteins via binding antibody multiplex assay (BAMA). Peptides corresponding to the V2-hotspot region of HIV-1 strains JR-FL-E168K (RDKVQKEYALFYKLD) (SEQ ID NO: 22), ADA (RDKVKKDYALFYRLD) (SEQ ID NO: 23), SF162P3 (GNKMQKEYALFYRLD) (SEQ ID NO: 18) were synthesized, microtiter plates were coated with 1 ug/ml of peptide at 4° C. overnight, and binding of macaque sera (1:100 dilution) was measured by ELISA (OD 450 reading).

Upon boosting with cycP-gp120 a strong cross-reactive antibody response against multiple clades of gp120 and gp140 antigens was observed, reacted to by all immunized animals. Responses were significantly higher in 15/16 of the antigens tested for needle-free orally immunized animals compared to ID/SC immunized at this time point (wk25), however at the pre-challenge time point both groups had similar levels of reactivity. These results show the high broadly-reactive antibody response generated by MVA/cycP-gp120 regimen. As results from the RV144 trial suggest that antibodies directed towards the V1V2 loop of gp120 are associated with reduced risk of infection, the generation of these antibodies, especially broadly reactive V1V2-directed antibodies, is of great interest in HIV-1 vaccine development.

To measure the cross-reactivity of V1V2-directed antibodies, sera IgG binding to a panel of 16 gp70-V1V2 scaffolds representing the global diversity of HIV-1 was quantified via BAMA. Two weeks post the first protein boost, needle-free SL/B immunized animals generated a substantial broadly cross-reactive gp70-V1V2 response against multiple clades of isolates, significantly higher than ID/SC immunization, demonstrating not only the high immunogenicity of the sublingual and buccal route, but also the broadening of the antibody responses upon needle-free oral delivery. Similarly, the anti-Env response at the pre-challenge time point responses to gp70-V1V2 scaffolds had contracted in both groups, with no significant differences between the groups, suggesting that through contraction and further boosting in ID/SC immunized animals the V1V2 response leveled to a set point.

To map the regions of gp120 targeted by the vaccine-induced antibody response, binding via peptide microarray of sera to 15-mer peptides (overlapping by 12 amino acids) derived from 13 strains including consensus clade B Env were measured. Both needle-free SL/B and ID/SC immunization resulted in a broad response against numerous regions of consensus clade B gp120, the strongest responses directed against the C1, C2, V3, and C5 regions of gp120. Binding responses against linear V2 hotspot epitope was developed against consensus B as well as to consensus A and CRF-01 AE, and clade C strain TV1 at lower magnitude (data not shown). Linear V2 binding was a subdominant response compared to V3 and C4 linear epitope binding. Comparing needle-free SL/B to ID/SC peptide responses showed similar trends in both groups, with a high proportion of the IgG response directed towards the C1, V3, and C5 regions, however needle-free SL/B immunization resulted in a modestly larger proportions of response against the V2, C4, V5, and C5.1 regions.

Antibody responses to the V2 Hotspot peptide were measured in a region of the V2 loop (spanning positions 166-178 of HIV-1 stain HXB2) in which antibody recognition correlated significantly with decreased risk of infection in the RV144 trial. Responses to the consensus B V2 peptides were detected in the peptide microarray analysis, primarily in the needle-free SL/B group, though these responses were modest compared to other regions. To determine responses to the V2-region of the vaccine and challenge virus strains, 13 amino-acid peptides were synthesized corresponding to the V2 hotspot of cycP-gp120 (clade-B JRFL, E168K), MVA-HIV (clade-B ADA), and SHIV-SF162P3 (clade-B). Needle-free SL/B immunization generated a strong cross-reactive V2 hotspot response, recognizing not only the MVA-HIV and cycP-gp120 vaccine strains (ADA, JRFL E168K), but also the heterologous SHIV13 SF162P3, similar to previous studies examining antibody responses generated by cycP-gp120. ID/SC immunization resulted in minimal V2 responses compared to needle-free SL/B immunization, which is likely due to the overall antibody response being significantly lower in ID/SC immunized animals at this time point. The cross-reactivity of V2 antibody responses to heterologous strains detected in both linear peptide microarray and in V2 hotspot ELISA demonstrates the remarkable ability of cycP-gp120 to generate V2-hotspot binding antibodies.

The generation of neutralizing antibodies to HIV-1 is a long-sought goal of HIV-1 vaccination. To test the presence of neutralizing antibodies generated by MVA-HIV/cycP-gp120 immunization, the neutralizing activity of sera was measured against a multi-clade panel of pseudoviruses that have high (SF162.LS, MW965.26), moderate (BaL.26), or low (ADA, JR-FL, TRO.11) neutralization sensitivity (tier-1A, -1B, -2, respectively). Needle-free SL/B immunization induced a significantly higher titer of neutralizing antibodies against the neutralization sensitive clade-B SF162.LS and the moderately resistant clade-B BaL.26 isolate after the first and second protein boosts than ID/SC immunization.

To evaluate non-neutralizing antibody effector functionality was characterized by antibody dependent phagocytosis (ADP), which measures the internalization of gp120-coated by monocytes via the binding of anti-gp120 IgG to Fc receptors, and antibody dependent cellular viral inhibition (ADCVI), which measures the combined ability of monocytes and Natural Killer cells (within human PBMCs) eliminate infected target cells (HIV SF162-infected CCR5+ CEM-NKr cells) and released cell-free virus in the presence of Env-specific antibodies.

In serum taken at pre-challenge, a range of ADP and ADCVI activity was measured in both vaccine groups, suggesting a breadth of effector functionality in the antibody response. Interestingly, when measuring ADCVI activity, sera from some animals enhanced viral outgrowth rather than inhibiting replication, whereas other sera inhibited up to 80% of viral outgrowth compared to controls (effectors+ targets+naive serum). ADCVI activity was not related to the magnitude of the antibody response at the pre-challenge time point, indicating that antibody effector functionality is more dependent on specificity than magnitude, and certain antibody responses may be detrimental in combating HIV-1.

Needle-Free SL/B Immunization Induces CD4 and CD8 T Cell Responses in Blood

To measure the cellular immune responses after immunization, peripheral blood mononuclear cells (PBMCs) were stimulated with HIV-1 clade B consensus Gag and Env peptides and cytokine production was measured in T-cells (Live CD3+ cells) by flow cytometry. Immunization with MVA-HIV resulted in IFN-γ production in CD4+ T-cells against both Gag and Env peptides, peaking one week after the second MVA-HIV immunization (wk16), and responses were similar between needle-free SL/B and ID/SC groups. Similar to IFN-γ responses, Gag and Env specific TNF-γ and IL-2 producing CD4+ T-cells were also observed, peaking again after the second MVA-HIV. Interestingly, unlike IFN-γ production, both TNF-α and IL-2 responses were expanded upon the first cycP-gp120+dmLT boost. In contrast to vaccine specific CD4 T-cell responses, only low levels of vaccine-specific CD8 T-cell responses were detected. They peaked after the second MVA-HIV immunization and contracted to below detection over the course of the immunization. However, vaccine-specific T-cell responses were not detected in the rectal or vaginal tissues after immunization, suggesting that stronger T-cell generating vaccine strategies, such as the utilization of DNA-primes, may induce these responses. As a major concern with HIV-1 vaccines is the unwanted generation of an abundance of HIV target CD4+ T cells in the mucosal tissue, the phenotypes of CD4 T-cells was characterized in rectal tissue at time of pre-challenge. Needle-free SL/B, topical SL/B, and ID/SC immunized animals all had similar levels of activated (HLA-DR+ CCR5+) CD4+ T-cells in the rectal tissue, indicating that immunization did not result in an accumulation of target cells in the rectal mucosa. Taken together, these data show that needle-free SL/B immunization is capable of generating vaccine-specific functional T-cell responses in the blood, similar to responses generated by conventional ID/SC immunization.

Figure 4A:
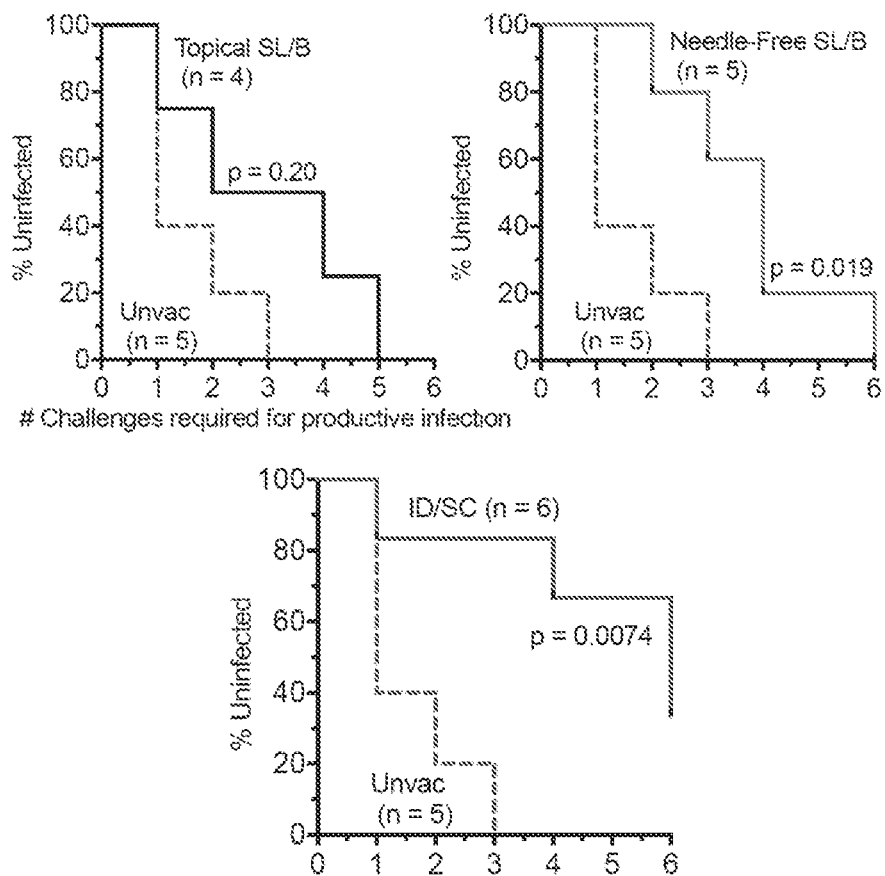
FIG. 4A shows data on the acquisition of infection in topical SL/B, needle-free SL/B, or ID/SC immunized animals indicating needle-free SL/B and ID/SC immunization induces delayed acquisition of heterologous SHIV-SF162P3 infection. Animals were challenged weekly with an intra-rectal low dose (1:100 dilution) of SHIV-SF162P3. Five unvaccinated macaques were used as a control. Vaccine efficacy of ID/SC, Needle-Free SL/B immunization vs control animals. Log-rank (Mantel-Cox) test.

MVA/CycP-Gp120 Vaccine Induced IgG Response Provides Significant Protection from SHIVSF162P3 Challenge in Needle-Free SL/B and ID/SC Groups As a preliminary readout of the efficacy of MVA-HIV/cycP-gp120 vaccine, animals were challenged 19 weeks after the second protein boost with repeat low-dose weekly intrarectal challenges of SHIV-SF162P3 for maximum of six exposures. The envelope in SHIVSF162P3 virus is a tier-2 Env, heterologous to the vaccine strains. No detectable neutralization was measured against this Env in vaccinated animals. Five unvaccinated female macaques were used as a control group. Following challenge, all unvaccinated animals were infected by the third challenge with 3 of the 5 becoming SHIV+ after the 1st exposure. Impressively, a significant delay in acquisition of infection was detected in both the needle-free SL/B immunized (p=0.019) and ID/SC (p=0.0074) immunized animals, but not topical SL/B immunization (p=0.20), with two ID/SC immunized animals remaining uninfected after the sixth challenge (FIG. 4A). Vaccine efficacy per exposure for each group was calculated to be 58% (Needle-Free SL/B) and 77% (ID/SC). No differences in vaccine efficacy were observed between these two vaccine groups. Tracking viral loads following infection, a trend was observed for lower set-point viral loads in immunized animals, but these did not reach significance.

Figure 4B:
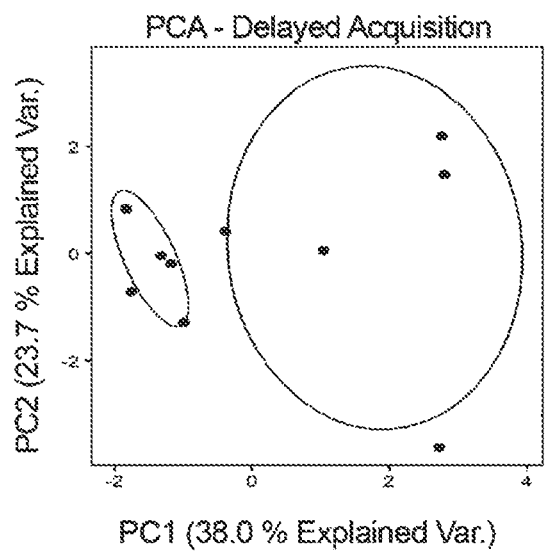
FIG. 4B shows results of Principal Comparison Analysis (PCA) plot indicating PC1 and PC2 scores for delayed (>=5 challenges) or non-delayed (<5 challenges) acquisition of infection in needle-free SL/B and ID/SC immunized animals.
Figure 5:
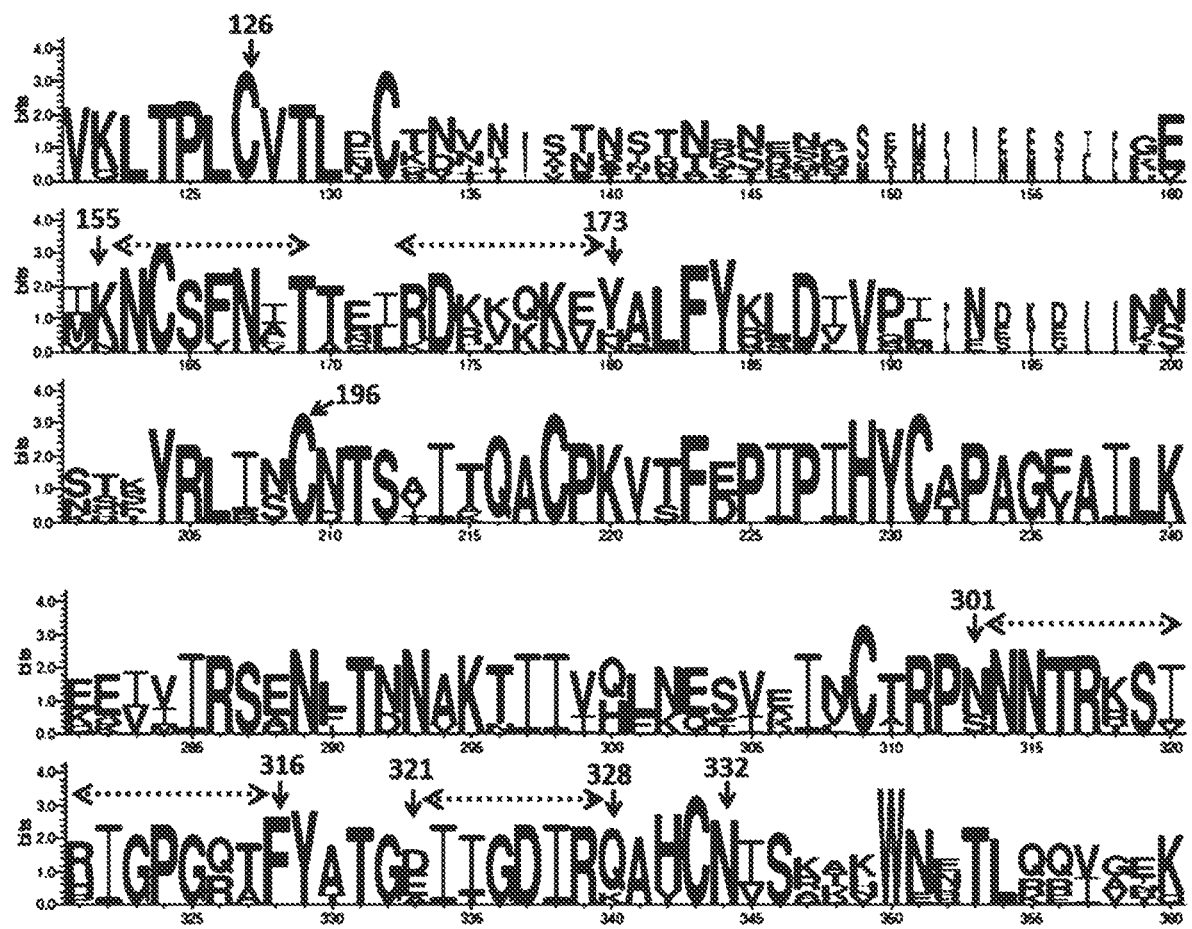
FIG. 5 illustrates conserved linear epitopes in the V2 and V3 regions of gp120 generated from multiple alignment of gp120 of Tier-2 HIV-1 isolates (SEQ ID NO: 24). The height represents its level of conservation at that particular position. The residue conservation at each position in the region V1V2 (residues 126-196) of gp120 is represented and the conserved linear epitope in the V2 region is indicated with a dotted arrow. The residue conservation at each position in the V3 region (residues 301-332) of gp120 is represented and the conserved linear epitopes are indicated with a dotted arrow. These conserved epitopes in the V2 and V3 region are surface accessible and immunodominant in nature.

Due to the low sample size in the vaccine groups, elucidating clear correlates of protection can be challenging. As both needle-free SL/B and ID/SC showed a significant delay in acquisition, as well as receiving the same vaccine immunogens, we combined the two groups for correlation analyses. To identify immune response profiles that could differentiate animals that showed delayed acquisition or were protected (>/=5 challenges) versus no delay in acquisition (<5 challenges), a principal component analysis (PCA) was performed with the immune responses measured in this study. PCA results showed that principal component 1 (PC1), containing ten variables, could separate animals with and without delayed acquisition (FIG. 4B), while a simulated PCA performed with the ten PC1 variables using randomized assay data showed no separation. Loadings for PC1 included CD4+ Env specific T cell responses, pre-challenge ADCVI activity, and V2 hotspot binding, as well as lower C5.3 linear epitope binding. Univariate analysis for these variables confirmed a significant positive correlation between the acquisition of infection and pre-challenge ADCVI activity, Env specific TNFα+CD4 T cells or Env-specific IFNγ+ TNF-α+ cells. There was a trend for positive correlation between the acquisition of infection and V2 hotspot binding. In addition, several parameters of the immune response correlated or highly trended with protection from infection, but these were observed only within single groups. These include the peak (wk25) serum IgG response, rectal IgG responses at pre-challenge, and the V2 hotspot response against the SHIV-SF162P3 challenge virus strain. Taken together, these data show that MVA-HIV/cycP-gp120 induced T-cell and antibody responses contribute to protection against pathogenic SHIV-SF162P3 infection.

---

The invention claimed is:

1. A method of vaccinating for HIV comprising:
   i) administering to a subject a nucleic acid and/or recombinant virus that encodes an HIV Env protein or segment thereof under conditions such that virus-like particles with surface gp120 proteins are formed in the subject;
   ii) administering to the subject an effective amount of a nucleic acid encoding a chimeric protein comprising an amino acid sequence selected from SEQ ID NO: 2, SEQ ID NO: 3, SEQ ID NO: 4, and SEQ ID NO: 5; and
   wherein administering is to the buccal cavity propelled through the skin or soft tissue lining of the mouth with pressure.

2. The method of claim 1, wherein administering to the subject an effective amount of the nucleic acid encoding the chimeric protein is more than one week after administering to a subject a nucleic acid or recombinant virus that encodes HIV Env protein or segment thereof.

3. The method of claim 1, wherein the subject is a human subject.

4. The method of claim 1, wherein the nucleic acid is RNA or DNA.

5. A composition comprising a nucleic acid encoding a chimeric protein comprising an amino acid sequence selected from SEQ ID NO: 2, SEQ ID NO: 3, SEQ ID NO: 4, and SEQ ID NO: 5.

6. The composition of claim 5, wherein the nucleic acid is RNA or DNA.

7. The composition of claim 6, wherein the nucleic acid is naked RNA or naked DNA.

* * * * *